(12) United States Patent
Thienphrapa et al.

(10) Patent No.: US 11,826,107 B2
(45) Date of Patent: Nov. 28, 2023

(54) REGISTRATION SYSTEM FOR MEDICAL NAVIGATION AND METHOD OF OPERATION THEREOF

(71) Applicant: KONINKLIJKE PHILIPS N.V., Eindhoven (NL)

(72) Inventors: Paul Thienphrapa, Cambridge, MA (US); Bharat Ramachandran, Morganville, NJ (US); Aryeh Leib Reinstein, Bronx, NY (US); Douglas Allen Stanton, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1192 days.

(21) Appl. No.: 16/064,164

(22) PCT Filed: Dec. 16, 2016

(86) PCT No.: PCT/IB2016/057699
§ 371 (c)(1),
(2) Date: Jun. 20, 2018

(87) PCT Pub. No.: WO2017/115201
PCT Pub. Date: Jul. 6, 2017

(65) Prior Publication Data
US 2019/0000562 A1    Jan. 3, 2019

Related U.S. Application Data

(60) Provisional application No. 62/272,178, filed on Dec. 29, 2015.

(51) Int. Cl.
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 90/39* (2016.02); *A61B 90/361* (2016.02);
(Continued)

(58) Field of Classification Search
CPC ......... A61B 34/20; A61B 34/30; A61B 90/39; A61B 2034/2048; A61B 2034/2051;
(Continued)

(56) References Cited

U.S. PATENT DOCUMENTS

| | | | |
|---|---|---|---|
| 6,529,765 B1 | 3/2003 | Franck et al. | |
| 9,110,156 B2 * | 8/2015 | Kim | G01N 29/44 |

(Continued)

OTHER PUBLICATIONS

Lu, T. et al., "Integration of the Image-Guided Surgery Toolkit (IGSTK) into the Medical Imaging Interaction Toolkit (MITK)". J. Digit Imaging (2012) 25:729-737.

*Primary Examiner* — Ashley K Buran
*Assistant Examiner* — Helene Bor

(57) ABSTRACT

A registration system for medical navigation includes a shape sensing device (SSD) (104, 504) having at least one sensor (450, 505) for providing corresponding sensor information (SI) indicative of at least one of a position of the at least one sensor (450, 505); a registration fixture (106) having a channel (130) configured to receive at least part of the SSD and defining a registration path (P). The registration fixture may be configured to be attached to a registrant object (RO) (119) defining a workspace. A controller (110) may be configured to: sense a shape of a path traversed by the SSD based upon the SI when the at least one sensor is situated within the channel (130), determine whether the sensed shape of the path corresponds with a known shape selected from one or more known shapes, and perform a coordinate registration based upon the determination.

19 Claims, 11 Drawing Sheets

(52) U.S. Cl.
CPC .......... *A61B 2034/2048* (2016.02); *A61B 2034/2051* (2016.02); *A61B 2034/2059* (2016.02); *A61B 2034/2061* (2016.02); *A61B 2090/3966* (2016.02)

(58) Field of Classification Search
CPC .... A61B 2034/2059; A61B 2034/2061; A61B 90/361; A61B 2090/3966; A61B 5/065; A61B 2526/0266; G01B 11/24; G01B 11/18
See application file for complete search history.

(56) References Cited

U.S. PATENT DOCUMENTS

| | | |
|---|---|---|
| 9,138,166 B2 | 9/2015 | Wong et al. |
| 9,285,246 B2 | 3/2016 | Prisco et al. |
| 9,757,034 B2* | 9/2017 | Desjardins ............ A61B 90/98 |
| 10,994,095 B2* | 5/2021 | Flexman ............... A61B 34/20 |
| 2002/0091319 A1* | 7/2002 | Moehring ............. A61B 8/463 600/454 |
| 2011/0113852 A1* | 5/2011 | Prisco .................. A61B 34/30 385/13 |
| 2011/0202069 A1* | 8/2011 | Prisco .................. A61B 34/71 606/130 |
| 2013/0028554 A1* | 1/2013 | Wong .................. G01B 11/24 385/12 |
| 2013/0276557 A1* | 10/2013 | Duindam ............. A61B 34/70 73/865.8 |
| 2013/0296691 A1 | 11/2013 | Ashe |
| 2013/0308137 A1* | 11/2013 | Manzke ................ G01B 11/24 356/511 |
| 2013/0317356 A1 | 11/2013 | Ramachandran et al. |
| 2014/0050375 A1* | 2/2014 | Baker .................. A61B 34/20 382/128 |
| 2014/0275997 A1* | 9/2014 | Chopra ................ A61B 34/30 600/424 |
| 2015/0193946 A1 | 7/2015 | Wong et al. |
| 2016/0157939 A1 | 6/2016 | Larkin et al. |
| 2016/0206384 A1 | 7/2016 | Dimaio et al. |
| 2016/0223753 A1 | 8/2016 | Noonan et al. |
| 2016/0331469 A1 | 11/2016 | Hall et al. |
| 2016/0363436 A1* | 12/2016 | Clark .................... G01L 1/246 |
| 2017/0014191 A1 | 1/2017 | Hautvast et al. |
| 2017/0265946 A1 | 9/2017 | Ramachandran et al. |
| 2017/0281282 A1* | 10/2017 | Noonan ............... A61B 17/154 |

* cited by examiner

REGISTRATION SYSTEM FOR MEDICAL NAVIGATION AND METHOD OF OPERATION THEREOF

CROSS-REFERENCE TO PRIOR APPLICATIONS

This application is the U.S. National Phase application under 35 U.S.C. § 371 of International Application Serial No. PCT/IB2016/057699, filed on Dec. 16, 2016, which claims the benefit of U.S. Patent Application No. 62/272,178, filed on Dec. 29, 2015. This application is hereby incorporated by reference herein.

The present system relates to a registration system using shape sensing methods and, more particularly, to coordinate system registration using Fiber Optic RealShape™ (FORS) or other tracking methods, such as electromagnetic (EM) tracking, for registering coordinate systems of one or more tracked devices using one or more registration fixtures to a reference coordinate system, and methods of operation thereof.

A surgical intervention comprises a number of components such as patient anatomy, operating table, imaging system(s), interventional devices, and models of any of these, be they preoperative images or software-rendered. Computer-assisted surgery (CAS) requires the disparate coordinate systems of some or all of these components to be registered, depending on the degree of assistance offered. For example, a device such as a surgical instrument must be registered to an imaging system to allow a model of the instrument to be properly displayed on the image. Such registration is useful especially when the device is difficult to discern in a raw image.

Registration can be performed preoperatively per procedure and may include a mechanically-tracked tool to sample multiple landmarks on the registrant object. Point-by-point acquisition of landmarks is time consuming, cognitively demanding, disruptive to workflow, and error prone. Although the registration procedure can be straightforward, it can also be cumbersome, particularly when problems arise that require re-registration which may be necessary due to changes in position of surgical equipment, support tables and/or a subject on a support table.

Further, in minimally invasive surgical procedures using catheters, needles or other flexible instruments, navigation of the flexible instruments inside the subject can be monitored using electromagnetic (EM) tracking to restore position information that can be lost to visual occlusion, such as when the flexible instruments are inserted in the subject. Because an EM field generator can be mounted in the workspace (e.g., operating table) in an unknown position, EM position information (e.g., generated by the EM field generator) is generally unaligned with a coordinate system of the table. In order for navigation to commence, positions in the EM space must be aligned, or registered, with those of the table or the patient/subject space. Methods currently used (such as feature-based methods that use corresponding point-based landmarks or models of shapes between two coordinate systems, or ways of associating EM position readings with corresponding information found through an imaging modality such as fluoroscopy) can be time consuming, cumbersome, and inconvenient especially during a surgical intervention.

Accordingly, embodiments of the present system may overcome these and other disadvantages of conventional registration systems.

The system(s), device(s), method(s), arrangements(s), user interface(s), computer program(s), processes, etc. (hereinafter each of which will be referred to as system, unless the context indicates otherwise), described herein address problems in prior art systems. Embodiments of the present system may employ shape sensing registration methods which may employ sample points, such as what may be considered a discretized set or a continuum of simultaneous sample points which may provide information related to a position of a coordinate system so that disparate coordinate systems may be registered.

In accordance with embodiments of the present system, there is disclosed a coordinate registration system, which may include a shape sensing device (SSD) having at least one position sensor for providing corresponding sensor information (SI) indicative of a position of the at least one position sensor. Alternately or in addition, the SSD may have sensor(s) that provide corresponding sensor information (SI) indicative of at least one of the position and an orientation of the at least one position sensor. The system may further include a registration fixture having a channel configured to receive at least part of the SSD and defining a registration path (P), the registration fixture may be configured to be attached to a registrant object (RO) defining a workspace; and/or a controller which may be configured to: sense a shape of a path traversed by the SSD based upon the SI obtained from the at least one sensor when the at least one sensor is situated within the channel (130), determine whether the sensed shape of the path corresponds with a known shape selected from one or more known shapes, and may perform a coordinate registration in when it is determined that the sensed shape of the path corresponds with the selected known shape.

It is further envisioned that the controller may interrogate the at least one sensor sequentially over time to obtain the SI. It is further envisioned that the at least one sensor of the SSD may include a plurality of sensors and, to obtain the SI, the controller may interrogate the plurality of sensors of the SSD synchronously over time. It is also envisioned that the controller may be further configured to: determine whether at least part of the SSD is within the channel; and may interrogate the SSD to obtain the SI from the at least one position sensor when it is determined that at least part of the SSD is within the channel. It is further envisioned that during the coordinate registration, the controller may be configured to determine a shape-to-fixture transformation ($^fT_s$) corresponding to the sensed shape. Further, during the coordinate registration, the controller may be further configured to obtain a fixture-to-workspace transformation ($^wT_f$) corresponding to the selected known shape. Moreover, during the coordinate registration, the controller may be further configured to determine a shape-to-workspace transformation ($^wT_s$) by calculating: $^wT_s = {^wT_f} * {^fT_s}$. In accordance with embodiments of the present system, the known path may be a registration path (P). It is also envisioned that the system may include an attachment or coupling mechanism for releasably attaching the registration fixture to the RO at one or more of a position and orientation relative to the workspace of the RO which corresponds with the fixture-to-workspace transformation ($^wT_f$).

In accordance with embodiments of the present system, there is further disclosed a method for registering coordinate systems, the method being performed by at least one controller. The method may include one or more acts of: interrogating at least one position sensor of a shape sensing device (SSD) to obtain sensor information (SI) indicative of a position of the at least one position sensor within a channel of a registration fixture coupled to a registrant object (RO) defining a workspace, the channel may be configured to receive at least part of a shape sensing device (SSD) and may define a registration path (P). Alternately or in addition, the obtained SI may be indicative of at least one of the position and an orientation of the at least one position sensor. The method may further include further acts of sensing a shape of a path traversed by the SSD based upon the SI obtained from the at least one sensor when the at least one sensor is situated within the channel; determining whether the sensed shape of the path corresponds with a known shape selected from one or more known shapes; and performing a coordinate registration when it is determined that the sensed shape of the path is determined to correspond with the selected known shape.

In accordance with embodiments of the present system, the act of interrogating may be performed sequentially over time. It is also envisioned that the at least one sensor of the SSD may include a plurality of sensors and the act of interrogating may be performed substantially synchronously over time. It is also envisioned that the method may further include determining whether at least part of the SSD is within the channel, and/or interrogating the SSD to obtain the SI from the at least one position sensor when it is determined that at least part of the SSD is within the channel.

In accordance with embodiments of the present system, the act of performing the coordinate registration may include an act of determining a shape-to-fixture transformation ($^{f}T_{s}$) corresponding to the sensed shape; and the act of performing the coordinate registration may include an act of selecting a fixture-to-workspace transformation ($^{w}T_{f}$) corresponding to the selected known shape; and/or the act of performing the coordinate registration may include an act of determining a shape-to-workspace transformation ($^{w}T_{s}$) by calculating: $^{w}T_{s}=^{w}T_{f}*^{f}T_{s}$. It is further envisioned that the method may include an act of inserting at least a portion of the SSD into the channel.

In accordance with embodiments of the present system, there is further disclosed a non-transitory computer readable medium comprising computer instructions which, when executed by a processor, may configure the processor to perform one or more acts of: interrogating at least one position sensor of a shape sensing device (SSD) to obtain sensor information (SI) indicative of a position of the at least one position sensor within a channel of a registration fixture coupled to a registrant object (RO) defining a workspace, the channel being configured to receive at least part of the SSD and defining a registration path (P). Alternately or in addition, the obtained SI may be indicative of at least one of the position and an orientation of the at least one position sensor. The computer instructions may further configure the processor to perform the further acts of determining a shape of a path traversed by the SSD based upon the SI obtained from the at least one sensor when the at least one sensor is situated within the channel; determining whether the sensed shape of the path corresponds with a known shape selected from one or more known shapes; and performing a coordinate registration when it is determined that the sensed shape of the path is determined to correspond with the selected known shape. It is also envisioned that processor may be further configured to perform an act of inserting at least a portion of the SSD into the registration channel. Further, it is envisioned that the act of interrogating the at least one position sensor of the SSD may be performed sequentially over time, when the at least a portion of the SSD is inserted into the registration channel.

The present invention is explained in further detail in the following exemplary embodiments and with reference to the figures, where identical or similar elements are partly indicated by the same or similar reference numerals, and the features of various exemplary embodiments being combinable. In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

For the sake of clarity, embodiments of the present system will be shown and described with respect to shape sensing devices (SSDs) such as shape sensing fibers. However, it is also envisioned that embodiments of the present system may be compatible with other tracking systems which may sample multiple data points sequentially or simultaneously. Further, it should be assumed that SSDs of the present system may be used alone or with a sheath such as a catheter, a guidewire, and the like.

Figure 1:
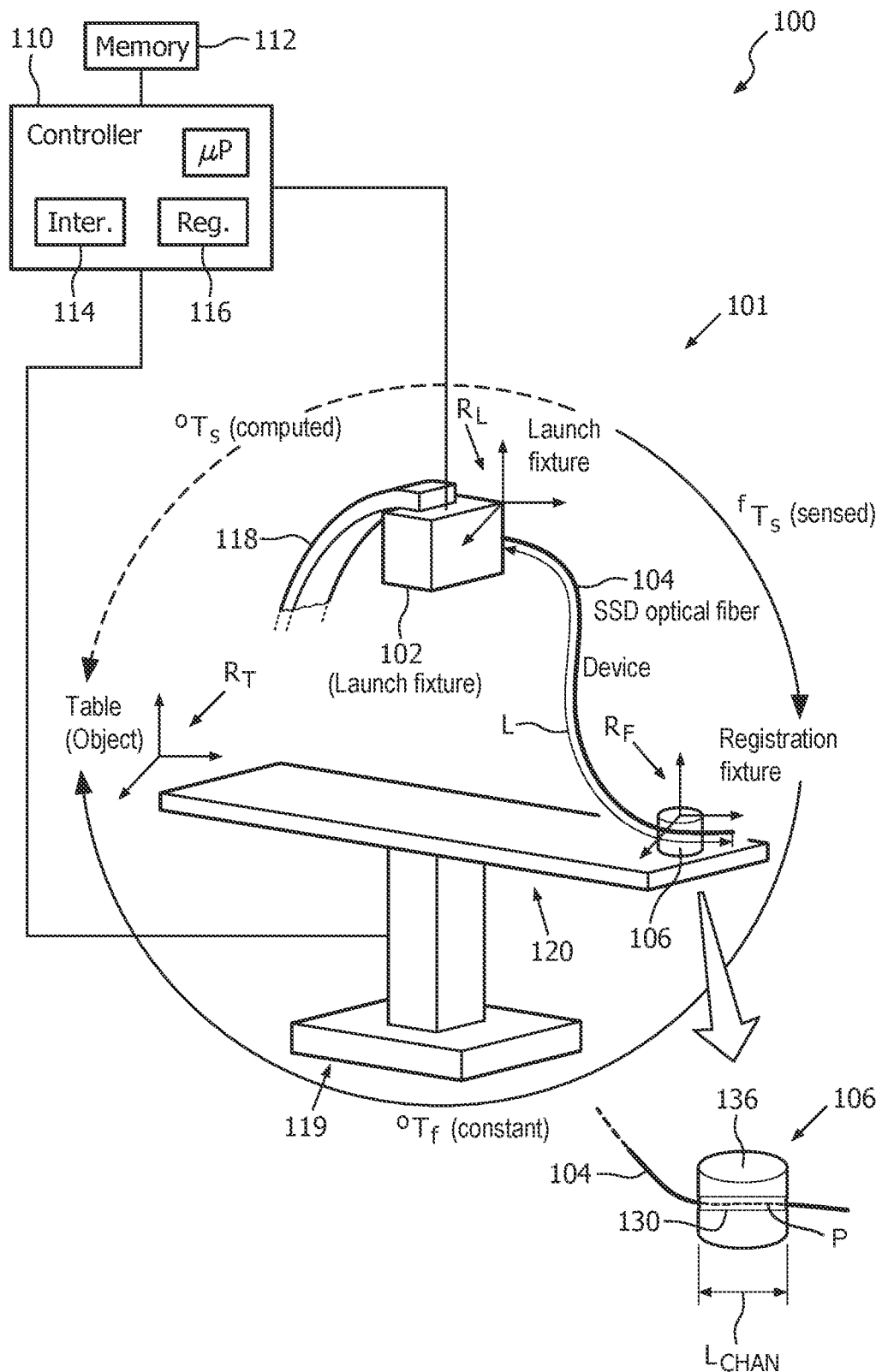
FIG. 1 shows a perspective front view of a portion of a registration system operating in accordance with embodiments of the present system.

FIG. 1 shows a perspective front view 100 of a portion of a registration system 101 (hereinafter system 101 for the sake of clarity) operating in accordance with embodiments of the present system. The system 101 may include one or more of a device base 102 such as a FORS launch fixture, an EM field generator, or a robot base, a shape sensing device (SSD) 104 such as a shape sensing fiber (SSF), a registration fixture 106 (hereinafter fixture unless the context indicates otherwise), a registrant object 119 (hereinafter RO or object unless the context indicates otherwise) such as a table 120, a controller 110, and a memory 112, one or more of which may be located locally and/or remotely from each other and may communicate with each other using any suitable wired and/or wireless communication link or links. For example, suitable communication links may include a local bus and/or a network (e.g., the Internet, a local-area-network (LAN), a wide-area-network (WAN), etc.).

The controller 110 may control the overall operation of the system 101 and may include one or more logic devices such as microprocessors (µP) having multiple interconnected semiconductor devices such as transistors, gates, impedance devices, metallization connections and the like, discrete and/or distributed logic gates and switching devices, and/or the like. The controller 110 may include an interrogation module 114 and/or a registration module 116 which may include hardware, software and/or firmware devices with instructions stored in a memory thereof and/or the memory 112, which when executed by the processor µP cause the processor to perform a desired functions.

The interrogation module 114 may be operative to obtain information from the SSD 104 (e.g., via an interrogation process) such as SSD information (SSDI) (which will be described below) and which may indicate a path travelled by the SSD over time and/or a shape of one or more portions of the SSD.

The registration module 116 may be operative to register the position and/or orientation of one or more ROs and/or coordinate system workspaces associated with the ROs such as a workspace ($R_T$) of the table 120 relative to a workspace ($R_L$) of the device base 102 based upon a workspace ($R_F$) of the registration fixture 106 as may be set forth in the SSDI which may include information related to a determined position and/or orientation of the registration fixture 106. Although a single RO such as the table 120 is shown and described in the present embodiments, for the sake of clarity, it should be understood that embodiments of the present system may be operative with other types and/or numbers or ROs. For example, in accordance with embodiments of the present system several ROs each with their own workspace may be used. Without limitation, it is envisioned that in accordance with embodiments of the present system, ROs may include an operating table, an imaging system, the anatomy of a patient, etc.

The memory 112 may include any suitable non-volatile memory in which information such as operating instructions, information generated by the system, user inputs and/or settings, historical information, operating settings and/or parameters, identification information, etc., may be stored. For example, the memory 112 may store information related to known shapes and associated transforms as may be discussed elsewhere.

The SSD 104 may extend from the device base 102 for a given length (L) and may provide signals such as SSDI indicative of its position and/or orientation along at least a portion of its length ($L_{ssd}$). The SSDI may further include information related to a shape of the SSD, if desired. The SSD 104 may be formed using any suitable shape sensing device such as a Fiber Optic RealShape™ (FORS) fiber or the like which may provide sensor information (e.g., SSDI) from a plurality of sensors indicative of position and/or orientation of a plurality of locations along its length $L_{ssd}$. The plurality of shape sensing locations may approach a continuum of locations, if desired. However, generally, the plurality of shape sensing locations may be set apart from each other by a desired distance such a 40 µm or other suitable distance. Suitable SSDs 104 may include, for example, a shape sensing fiber (SSF), an EM-based tracking device with at least one EM sensor such as an EM sensor located at a tip thereof, etc., and/or combinations thereof, such as described in U.S. Patent Application Publication No. 2013/0317356 to Ramachandran et al., which is incorporated herein by reference in its entirety, where the position and/or orientation sensors may be active light emitting diodes, passive reflectors such as spheres, optical and/or EM coils, and/or radioactive or radiopaque markers which are identifiable based on imaging such as X-ray and/or nuclear based imaging. Similarly to the optical sensors, the EM sensors and/or other sensors/markers may be situated at one or more locations apart from each other as may be desired, or a shape can be reconstructed from a single point sensor by accumulating a history of positions as the SSD is passed through a path.

In use, the SSDI may be obtained by interrogating the SSD 104. The interrogation may employ optical and/or EM interrogation techniques which may correspond with a type of the SSD employed by the system. For example, the SSF may employ Fiber Optic RealShape™ (FORS) interrogation techniques to determine position and/or orientation thereof, while the EM-based tracking device may employ EM interrogation methods to obtain the SSDI. However, it should be understood that these interrogation techniques may or may not be exclusive of each other. Further, the optical interrogation technique may interrogate at least one optical sensor of the SSD synchronously in time and the EM interrogation technique may interrogate at least one EM sensor of the SSD sequentially in time and/or vice versa.

Regardless of the type of interrogation technique, the interrogation may obtain the SSDI which may then be processed to perform a registration of an SSD to a reference workspace coordinate system (e.g., $R_T$) as may be described elsewhere in this application. The controller 110 may be communicatively coupled (using any suitable method such as electronically, optically, etc.) to the SSD 104 so that the SSD 104 may be interrogated. For the sake of clarity, it will be assumed that the workspace of the RO may be referred to as a reference workspace. However, it should be understood that there may be several reference workspaces in a system operating in accordance with embodiments of the present system.

The device base 102 may be positioned in a suitable position and/or orientation such as in fixed and/or variable positions as may be desired. For example, the device base 102 may be coupled to any suitable base 118 such as to the table 120, to a C-arm-type base such as used for X-ray imaging, and/or to any other suitable base, which may locate the device base 102 in a desired position and/or orientation such as above the table 120, at the table, next to the table, etc. However, it is also envisioned that the device base 102 may be located in other locations such as under the table 120, to a side of the table 120, etc. Regardless of the position and/or orientation of the device base 102, the system may perform a registration of the device base 102 to the object or workspace (e.g., table 120), which contrasts with conventional methods in which a position and/or orientation of a device base must be accurately known for proper registration to a reference frame, or with conventional feature-based registration methods that require acquisition of multiple point samples, thus multiple steps to execute and possibly multiple operators to perform. Thus, a location of the device base 102 does not have to be explicitly known to the system to perform a registration in accordance with embodiments of the present system. This may simplify surgical routines as the device base may be moved intraoperatively and may be easily and conveniently re-registered to a reference workspace by the system. Thus, the device base 102 may positioned, such as clipped to the table 120, at a convenient location such as near an incision site where a distal end of a catheter (needle, and/or other flexible instruments) having its proximal end attached to the device base 102 may be inserted into the incision site of a subject positioned on the table 120. Accordingly, an accurate determination of the positioning of the device base 102 prior to catheter insertion is no longer needed as registration is simplified by insertion of the SSD 104 into the RC 130 of the fixed registration fixture 106.

The device base 102 may include a coupling for receiving the SSD 104 and/or for positioning and/or orientating the SSD 104 in any desired position and/or orientation relative to the RO such as the table 120. It is envisioned that the device base 102 may include a plurality of these couplings each for receiving a corresponding SSD 104 of a plurality of SSDs 104. However, as each of these couplings may be similar to each other, reference will only be made to a single coupling for the sake of clarity. Further, the device base 102 may be operative as a base for one or more other implements such as catheters and the like for insertion into in incision site of a subject positioned on the table 120.

It is envisioned that the device base 102 may further include a plurality of catheters affixed thereto. Each catheter may include one or more channels to receive corresponding SSDs such as the SSD 104, if desired. For example, it is envisioned that the SSD 104 may be situated, at least in part, within a catheter, if desired and/or situated along and/or attached to an outer surface of the catheter. In accordance with some embodiments, the device base 102 may include one or more sensors which may detect position and/or orientation of the SSD 104 extending therefrom.

The base 118 may be fixed and/or movable as may be desired. The base 118 may include a C-arm or the like, as may be desired. For example, the base 118 may be moved during use, if desired.

The table 120 may include any suitable platform to which the registration fixture 106 may releasably and/or fixedly coupled. Accordingly, the table 120 may include one or more couplers which may couple to the registration fixture 106 in a known position and/or orientation relative to the table 120. This known position may have a corresponding fixture-to-workspace transformation ($^wT_f$) and may be stored in a memory of the system in association with a corresponding fixture-to-object pair (FOP), e.g., fixture 106 to table 120 in the present embodiments, and may be obtained from the memory when performing a registration. Thus, as the position of the registration fixture 106 to the workspace (e.g., of the RO such as the table 120) for a particular FOP is known (e.g., with respect to one or more axis and/or coordinates that indicate position and/or orientation), $^wT_f$ may be known and stored in a memory of the system for later use such as when performing a registration process. Although there may be a plurality of fixture-to-object pairs (FOPs), for the sake of clarity, only a single fixture-to-object pair will be discussed.

The RO may have its own workspace which may define its own workspace coordinate system $R_L$. For example, with regard to the table 120, the table 120 may have its own workspace $R_t$ which may be the same as or different from $R_L$. However, for the sake of clarity, it will be assumed that $R_t$ and $R_L$ will be different from each other.

The table 120 may include actuators controlled by the controller 110 which may vary position and/or orientation of the table 120 and/or portions thereof under the control of the controller 110. The table 120 may further include sensors which may provide information related to position and/or orientation of one or more portions of the table 120.

Although the RO is illustrated as a table 120 (e.g., an operating room table), in accordance with yet other embodiments, the RO may include other objects such a patient, imaging system, etc., as may be described elsewhere in this document.

The registration fixture 106 may include one or more of a body 136, an attachment mechanism such as a coupler, and at least one registration channel (RC) 130, the latter of which may define a path (P) having a length ($L_{chan}$) such as 7 cm in the present embodiments, however other lengths are also envisioned. The RC may be configured to receive the SSD 104 for use such as during a registration.

The attachment mechanism may be configured to attach the registration fixture 106 to a desired object for registration such as the table 120 in the present embodiments. However, it is also envisioned that the coupler may be configured to attach the registration fixture 106 to one or more other objects for registration of these other objects. Further, the coupler may include releasable or non-releasable couplers, if desired.

Figure 2:
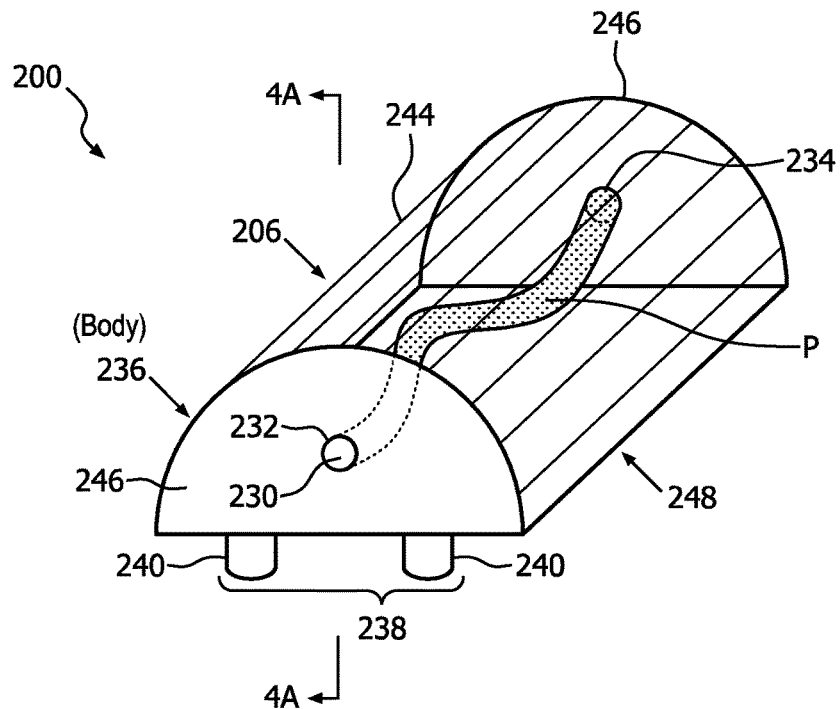
FIG. 2 shows a perspective front view of a portion of a registration fixture in accordance with embodiments of the present system.

FIG. 2 shows a perspective front view 200 of a portion of a registration fixture 206 in accordance with embodiments of the present system. The registration fixture 206 may be similar to the registration fixture 106 and may include one or more of a body 236, an attachment mechanism 238, and at least one RC 230 extending through the body 236.

The RC 230 may extend between end openings 232, 234 and have a predefined shape so as to define a known path (P) with a length ($L_{chan}$) for insertion of the SSD 104 through either one of the end openings 232, 234. Alternatively, the RC 230 has a single opening at one end for insertion of the SSD 104 into the RC 230 until the SSD 104 reaches the other closed end of the RC 230. The path (P) may be asymmetric to facilitate computation of the registration. The RC 230 may be shaped, sized and/or otherwise configured to receive an SSD 104 such that the SSD 104 may extend, at least partially through the RC 230, with a snug fit so that sensory positions of the SSD 104 within the RC 230 may have a known position and/or orientation relative to the RC 230 when interrogated thus allowing determination of the shape of portion of the SSD 104 inserted or located in the RC 230. The path (P) of the RC 230 may be open to design based on requirements of accuracy, space/size constraints, friction, etc. For example, a long and/or intricate path may lead to improved registration accuracy, but may require excessive length or tortuosity from the RC 230 of the SSD. Accordingly, the length ($L_{chan}$) and/or the shape of the path (P) may be set according to application and/or use. Further, each RC 230 may have a unique path for easy identification, if desired. The RC 230 may have a cross-section having any suitable shape such as circular, elliptical, square, polygonal, etc. In accordance with embodiments of the present system, the RC 230 may alternatively have one or more openings to define a C- or U-type channel cross-section (e.g., to form a groove) at any desired cross-sectional location along the path (P). It is further envisioned that the channels in embodiments of the present system may include an opening extending along a length thereof so that an SSD or parts thereof (e.g., a tip) may be inserted within the channel. The RC 230 may include a friction reducing interior surface and/or friction increasing surfaces so as to attain desired amount of friction when the SSD 104 is inserted within the RC 230 during use.

Accordingly, depending upon a type of interrogation used by embodiments of the present system, the SSD 104 may be positioned within an RC 230 for interrogation by inserting the SSD 104 into an opening of the RC 230, clipping the SSD to the RC, touching the SSD to the RC, sliding the SSD against the RC, etc. The SSD may be positioned statically or dynamically within the RC for interrogation. For example, an optical interrogation technique may interrogate the SSD 104 after it has been placed in the RC 230 and may remain static while an EM interrogation technique may interrogate the SSD 104 as it is advanced into the RC 230 and/or retracted from the SSD 104.

It is further envisioned that RCs may include one or more open sides and/or attachment portions which may couple an SSD in a desired position relative to the RC during use. For example, the RC may include clips, magnetic portions, "C" channels, etc., which may hold the SSD in, or to, a desired path of the RC during use.

The body 236 may have a shape and/or size so as to receive and/or otherwise support the RC 230 in a desired position and/or orientation relative to the body 236. For example, a half-cylindrical body in which the RC 230 may be situated is shown for the sake of illustration. Accordingly, the body 236 may include opposed ends 246, rods 244, and a base 248. The rods 244 may extend between and be coupled to the exposed ends 246. The base 248 may provide a support platform and may be coupled to the opposed ends 246.

However, in accordance with embodiments of the present system, the body 236 may include other shapes and/or may include solid body (e.g., a solid block of material, etc.) in which the RC may be located. In accordance with some embodiments, it is also envisioned that the RC may be formed integrally with the body.

The attachment mechanism 238 may include one or more couplers suitable for coupling to a desired RO such as the table 120 in the present embodiments. Thus, the registration fixture 206 may be associated with a workspace of the RO.

For the sake of clarity, the table 120 may be substituted for the RO herein. However, it should be understood that other ROs such as imaging systems, patient supports, etc., may be substituted for the table 120, if desired. The attachment mechanism 238 may correspond with a corresponding attachment mechanism (e.g., a coupler) of the RO and may locate the RC 230 in a desired position and/or orientation relative to the RO to which the registration fixture 206 is coupled. Thus, the attachment mechanism 238 may be configured to correspond to a coupler of an RO to which coupling may be desired and may hold the registration fixture 206 (or portions thereof) in a desired position and/or orientation relative to one or more portions of the RO to which it is coupled.

With regard to the attachment mechanism 238, a suitable coupler may include one or more lugs 240 (e.g., mounting pegs which may be splined or keyed to maintain orientation, if desired) which may engage a corresponding portion (e.g., an opening which may be correspondingly splined and/or keyed, if desired) of the table 120 so as to hold the registration fixture 206, and, thus, the RC 230 in a desired position and/or orientation relative to the RO. Accordingly, when attached at a desired position and/or orientation, the RC 230 has a known relationship to the table 120 and, thus, to the workspace of the table.

In accordance with further embodiments, it is envisioned that the attachment mechanism or mechanisms may include other types of couplers such as interlocking groves, patterns, and/or mechanisms, screwable-type couplers, bayonet mounts, friction mounts (e.g., snap-on type couplers), adhesives, bonds, rivets, etc., which may be releasable and/or non-releasable, as may desired. It is further envisioned that an RC 230 may be formed integrally with the RO, if desired.

Regardless of a type of attachment mechanism employed (e.g., fixed and/or removable), the attachment mechanism, when secured, should locate the registration fixture 206 in a desired position and/or orientation relative to the registrant object (e.g., the table 120) such that may correspond with a previously determined fixture-to-workspace transformation ($^wT_f$). The fixture-to-workspace transformation ($^wT_f$) may be determined mathematically and/or through actual measurement and may be stored in a memory of the table for future use such during a registration process. In other words, the registration fixture 206 may be located such that its position and orientation (e.g., for 6D localization=3D position and 3D orientation), or position or orientation (e.g., 3D localization) relative to an RO may be known.

In accordance with embodiments of the present system, an orientation-only (e.g., 3D) or standard registrations (e.g., 6D) may be performed in accordance with user and/or system settings. Orientation-only registrations may register orientation (3D) (as opposed to location/position) of coordinate systems, while standard registrations may register location/position as well as orientation (e.g., 6D=3D+3D). Accordingly, when using orientation-only, image information and, thus, corresponding images, may be correctly oriented but shifted from that of a reference coordinate system.

Figure 3:
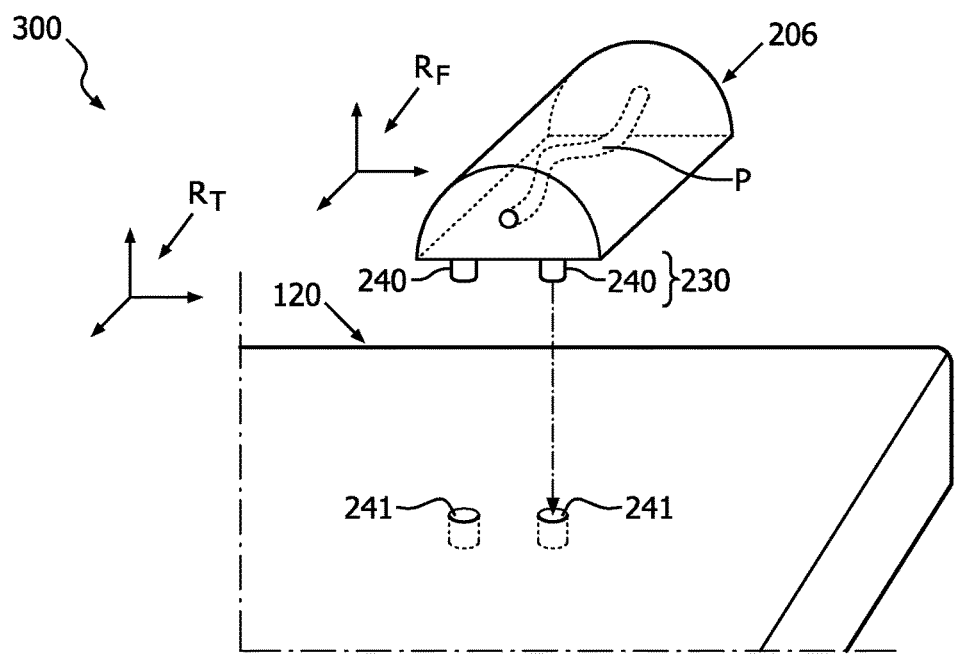
FIG. 3 shows an exploded perspective view of a portion of the registration fixture coupling to the table in accordance with embodiments of the present system.

FIG. 3 shows an exploded perspective view 300 of a portion of the registration fixture 206 coupling to the table 120 in accordance with embodiments of the present system. The lugs 240 may be asymmetrically located relative to the registration fixture 206 and inserted into corresponding openings 241 in the table 120 such that the registration fixture 206 may be located in a desired position and/or orientation relative to the table 120 when properly attached. Accordingly, a relationship between a workspace of the registration fixture $R_F$ and table $R_T$ for the corresponding FOP at a corresponding mounting location may be constant and, once determined, may be stored in a memory of the system for later use such as during a registration process performed in accordance with embodiments of the present system.

Figure 4A:
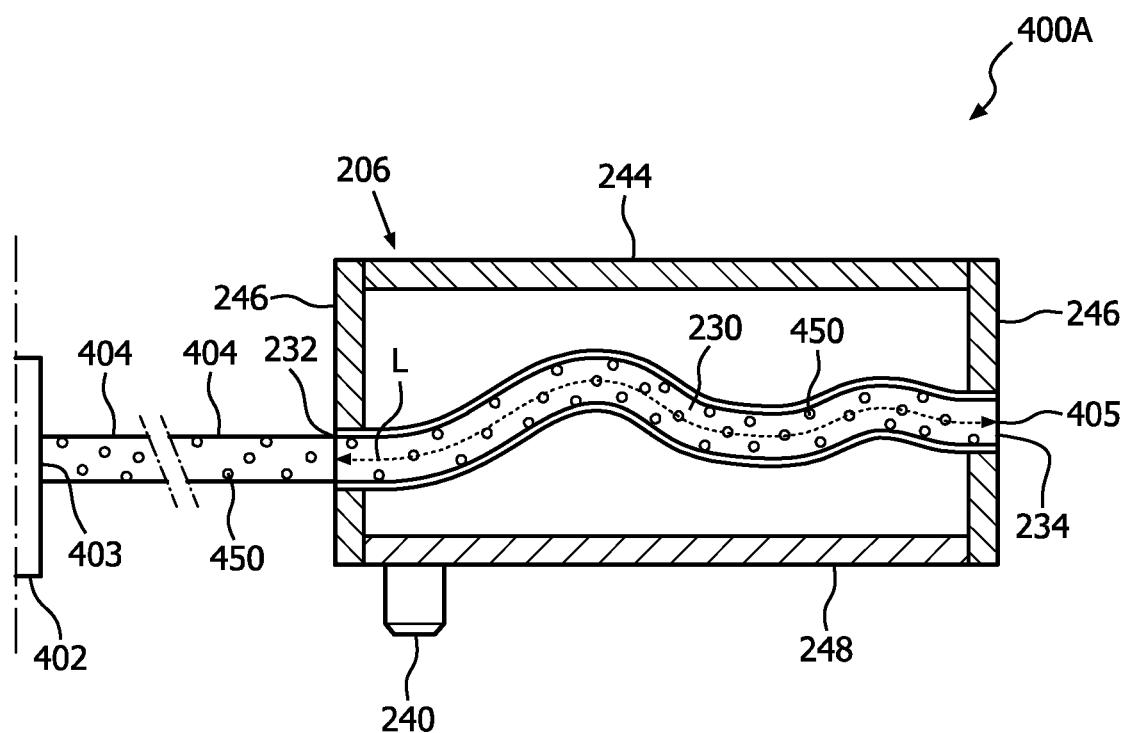
FIG. 4A shows a cross sectional view of a portion of a registration fixture taken along lines 4A-4A of FIG. 2 in accordance with embodiments of the present system.

FIG. 4A shows a cross sectional view 400A of a portion of a registration fixture 206 taken along lines 4A-4A of FIG. 2 in accordance with embodiments of the present system. An SSD 404 (which may be similar to the SSD 104) may be attached from the proximal end of an SSD to a device base 402 (which may be similar to the device base 102) and may extend through the RC 230 such that a proximal end 403 of the SSD 404 is adjacent to the device base 402 and a distal end 405 of the SSD 404 is adjacent to, or may extend from, one of the end openings 232, 234 of the RC 230.

To perform a registration, the SSD 404 may be inserted through one of the at least one end openings 232, 234 of the RC 230 and may exit through the other of the at least one end openings 232, 234 as shown. However, it is also envisioned that the SSD 404 may be situated within the RC 230 and may end at, or before, the other of the at least one end openings 232, 234, if desired. Alternatively, the registration fixture 206 may only have a single opening 232 at its proximal end for insertion of the SSD 404, and may have a closed distal end that stops travel of the inserted SSD 404 once it reaches the closed distal end of the registration fixture 206. Alternatively, the SSD 404 may be inserted into the registration fixture 206 in a relaxed configuration, and a clamping mechanism within the registration fixture 206 is engaged that configures the portion of the SSD 404 within the registration fixture 206 into the desired known path. The SSD 404 may include a plurality of sensors which may provide information related to the position and/or orientation of the SSD 404 so that a path (P) of the RC 230 may be determined from SSDI obtained from the SSD 404. The sensors may be placed at desired locations such as evenly displaced along a length of the SSD 404, etc. Depending upon system design, the sensor may include EM sensors, optical sensors, or the like and may depend upon a type of interrogation system being employed (e.g., EM and/or optical). For example, the sensors may include optical sensors 450 illustrated as "o"s which may provide optical sensor information when interrogated.

With regard to interrogation, the plurality of sensors and may be distinguishable by sensor, if desired. The system may distinguish between these sensors so as to select a subgroup of sensors to receive sensor information from the group of sensors. Accordingly, by selecting subgroups of sensors from which sensor information is to be received, a subset of points along a length of the SSD 404 may be selected. For example, registration may be accomplished using all the sensors of the SSD 404 or a subset of the sensors and, thus, a subset of points along a path of the SSD 404 located within the registration fixture 206. The subset of points may be selected so that they are uniformly distributed (e.g., spaced evenly) or spaced via some physical criteria. For example, assuming that the path (P) of the RC 230 within the registration fixture 206 is shaped like a sine wave (in 2D or 3D), the subset of points along the path selected for registration can be those that are on the peaks of the humps, or those which are on the inflection points (e.g., when the sine wave transitions from concave up to concave down). This may simplify computation. For example, for a full-path method (e.g., using sensor information from a group of all the sensors), the process may employ an algorithm such as an Iterative Closest Point, a template matching method, or the like, which are well known in the art. However, for a subset-of-points method (e.g., using SSDI from a selected subset of sensors of the group of sensors), the process may employ an algorithm such as a point-based algorithm such as Procrustes, least squares optimization, or the like, which are well known in the art.

Figure 4B:
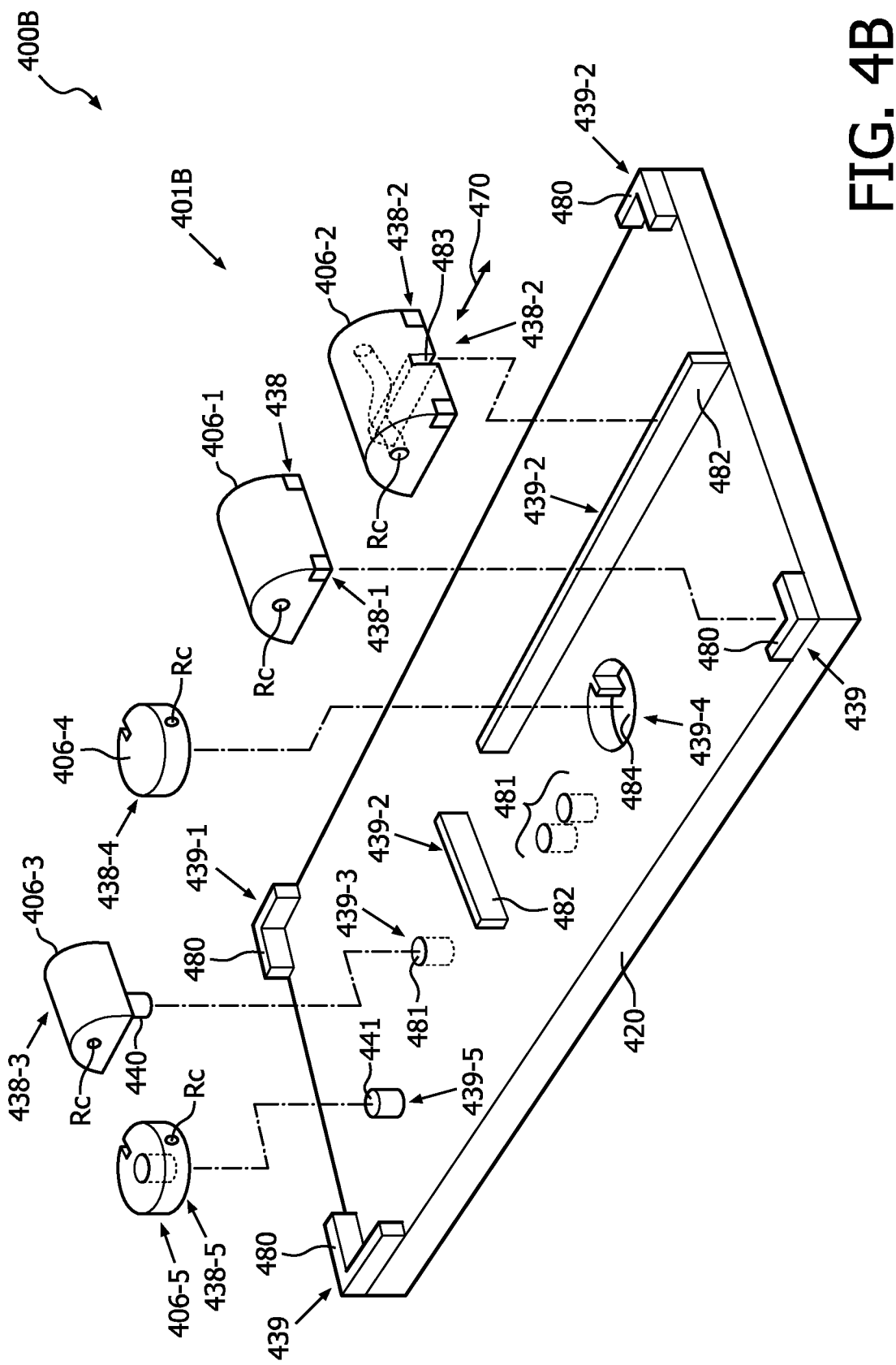
FIG. 4B shows a perspective view of a portion of a registration system in accordance with embodiments of the present system.

FIG. 4B shows a perspective view 400B of a portion of a registration system 401B (hereinafter system 401B) in accordance with embodiments of the present system. The system 401B may be similar to the system 101 and may include a plurality of registration fixtures 406-1 through, 406-M (where M is an integer, generally 406-x) each of which may be operatively similar to the registration fixture 106 and may be coupled to an RO (e.g., table) 420. The RO 420 may have a plurality of attachment mechanisms 439-1 through 439-N (where N is an integer, generally 439-x) each of which may couple to corresponding attachment mechanisms 438-x of corresponding registration fixtures 406-x.

Although a plurality of attachment mechanisms 438 is shown for illustration, only a single corresponding attachment mechanism pair 438-x and 439-x may be required to couple to a single registration fixture 406-x to perform a registration. The attachment mechanisms 439-x types may include, for example, corner flanges 480, flanges 482, openings 484, opening pairs 481, pegs 441, etc. which may couple to corresponding attachment mechanisms 438 of one or more registration fixtures 406-x. For example, corner flanges 438 of registration fixture 406-1 may couple to corner flanges 480 of the RO 420, RO openings 484 (may be keyed) may receive lugs 440 or a body of a corresponding registration fixture 406-x (each of which may be keyed, if desired), RO flanges 482 may receive fixture keyways 483, etc. With regard to the RO flanges 482, when coupled to the keyways 483 of the registration fixture 406-1, the registration fixture 406-1 may move laterally as shown by arrows 470. Accordingly, a corresponding registration fixture (e.g., 406-2) may be used for orientation-only registration.

With regard to orientation-only registration methods, these methods may provide a registration solution that may be valuable even if it provides only rotational alignment. The remaining translational offset may be easier to resolve and can be accomplished, for example, via simple drag-and-drop or left/right/up/down shift operations in software, or in presentation as a side-by-side display rather than a traditional overlay commonly found in surgical or global-positioning system (GPS) navigation. It is further envisioned that relative navigation, e.g., "turn right in 4 meters and proceed for 10 feet," may then become possible. This may, for example, reduce processing computations when translational offset may not be required. Other scenarios that benefit from an orientation-only registration may include, without limitation, prototyping in image-guided interventional systems and robotics, where sequences of events may be executed outside the actual workspace for simulation and testing purposes.

When using orientation-only registration, embodiments of the present system may provide a registration fixture fabricated in a form factor that may: (1) allow a registration fixture to be aligned to a workspace in an intuitive way; and (2) may suggest the registration fixture's local coordinate system implicitly, explicitly, or both. For example, a registration fixture with right angles can be used for orientation-only registration of objects with right angles such as tables, walls, bridges, and/or other structures. A registration fixture (such as the registration fixture 406-1 of FIG. 4B) may be placed on a table with one corner and two edges of the fixture coincident with the same from the table. Desired orientation such as XYZ axis orientation of the registration fixture may be displayed using graphical methods (such as labels or other documentation) and/or mechanical interlocks (e.g., of the coupling mechanism) so placing the registration fixture on the table in the desired orientation, and then inserting an SSD through a registration channel of the registration fixture for registration, creates an XYZ coordinate system for the table in a shape sensing device world. Moving the registration device along the length of the table becomes equivalent to moving in the Z-direction, moving across the table becomes equivalent to moving in the X-direction, and moving up/down becomes equivalent to moving in the Y-direction. A device base (i.e., where the catheter's proximal end is attached to the device base) may no longer need to be aligned with the table; in general, even if a launch is aligned by chance with one registrant object, it is unlikely to be aligned with others. This orientation-only registration capability may be useful for rapid prototyping of computer-assisted navigation systems, and the remaining translational offset may be easily managed as mentioned above—a hybrid registration approach.

Figure 4C:
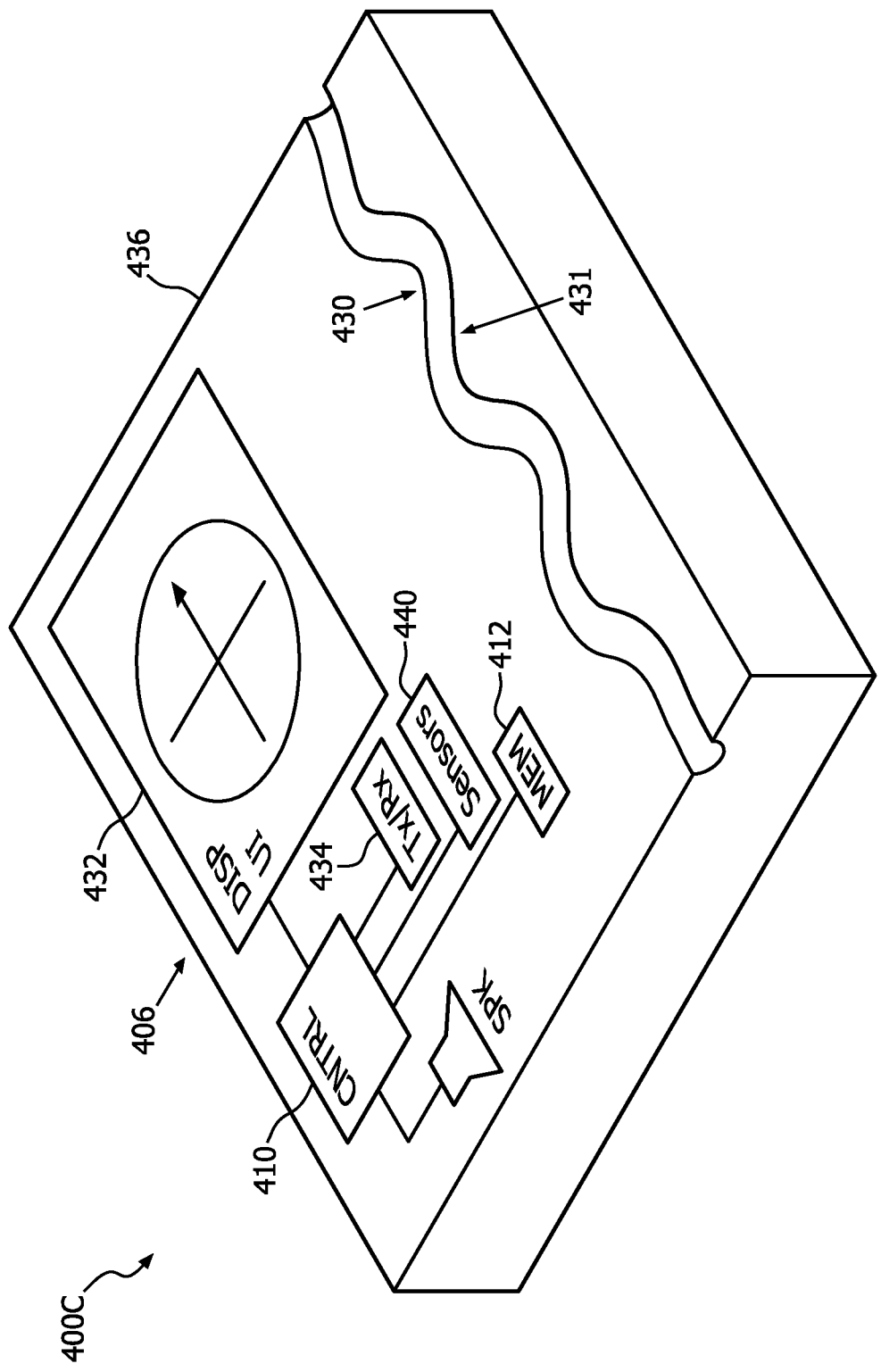
FIG. 4C shows a perspective front block diagram view of a portion of a registration fixture in accordance with embodiments of the present system.

FIG. 4C shows a perspective front block diagram view 400C of a portion of a registration fixture 406 in accordance with embodiments of the present system. The registration fixture 406 may be similar to the registration fixture 106 and may include one or more of a body 436, an attachment mechanism, and at least one RC 430, a controller 410, sensors 440, a memory 412, a transmitter/receiver (Tx/Rx) 434, and a user interface (UI) such as a display 432 and/or a speaker (SPK). The RC 430 may include a channel having a path (P) and may include identifying marks such as protrusions 431 which may further identify the RC (e.g., in addition to an identity of the path (P)). The controller 410 may control the overall operation of the registration fixture 406. The Tx/Rx 434 may receive information from the controller 410 for transmission, and may receive information transmitted and provide this received information to the controller 410 for further processing. The sensors 440 may include at least one sensor which may detect position and/or orientation of the registration fixture 406 relative to an external reference system such as a universal reference system, a radio wave positioning system (e.g., a GPS positioning system, a triangulation system, etc.), an optical positioning system (e.g., using optical alignment techniques), a magnetic positioning system (e.g., the Earth's magnetic field, a main magnetic field of an MRI, etc.), a mechanical positioning system (e.g., by sensing coupling to the mechanical positioning system such as coupling to lugs, receiving lugs, flanges, etc.), a gravitational positioning system (e.g., Earth's gravitational field, etc.), etc. and form corresponding position information (which may include orientation information), and provide this information to the controller 410 for further processing. The controller 410 may then process the position information to determine the position and/or orientation (depending upon system settings) of the registration fixture 406 and provide this information (e.g., via a wired and/or wireless transmission via the Tx/Rx 434) to external devices (e.g., a client) which may be in communication with the registration fixture 406. Further, the controller 410 may be operative to render information generated by the controller 410 on the UI such as on the display 432 and/or speaker (SPK) such as position and/or orientation information, communication information, etc.

Thus, registration fixtures may include a controller and at least one sensor which may detect the orientation of the registration fixture and provide this information to the controller so that information related to the corresponding registration fixture may be provided to a system controller of a system in which the registration fixture is situated. Accordingly, registration fixtures may provide information to indicate their orientation with respect to a universal reference system (e.g., the physical world), allowing for orientation-only registration with respect to a cardinal direction (north, south, east, and west), gravity, floors, etc. In the absence of obvious coordinate systems in the workspace, the ability to perform rough navigation with respect to some global reference such as those mentioned may be useful; examples may include system prototyping and relative navigation scenarios where full registration may not be critical. Sensors and measurement devices that may be integrated into the registration fixture to assist in finding reference frames may include any suitable sensor such as: a compass, a level, a ruler, a caliper, an accelerometer, a magnetometer, a protractor, a GPS locator, an orientation sensor, a light sensor, a range finder, a gyroscope, a radar, a sonar, etc., sensors. In accordance with embodiments, it is further envisioned that a registration fixture may further include a rendering device such as a display, a speaker, etc., which may render information generated by the controller which may be render orientation, distance measurements, etc. for the convenience of the user. Further, it is envisioned that registration fixtures may include a communication interface which may be operative to relay information from the sensors to client systems under the control of a controller.

Figure 5:
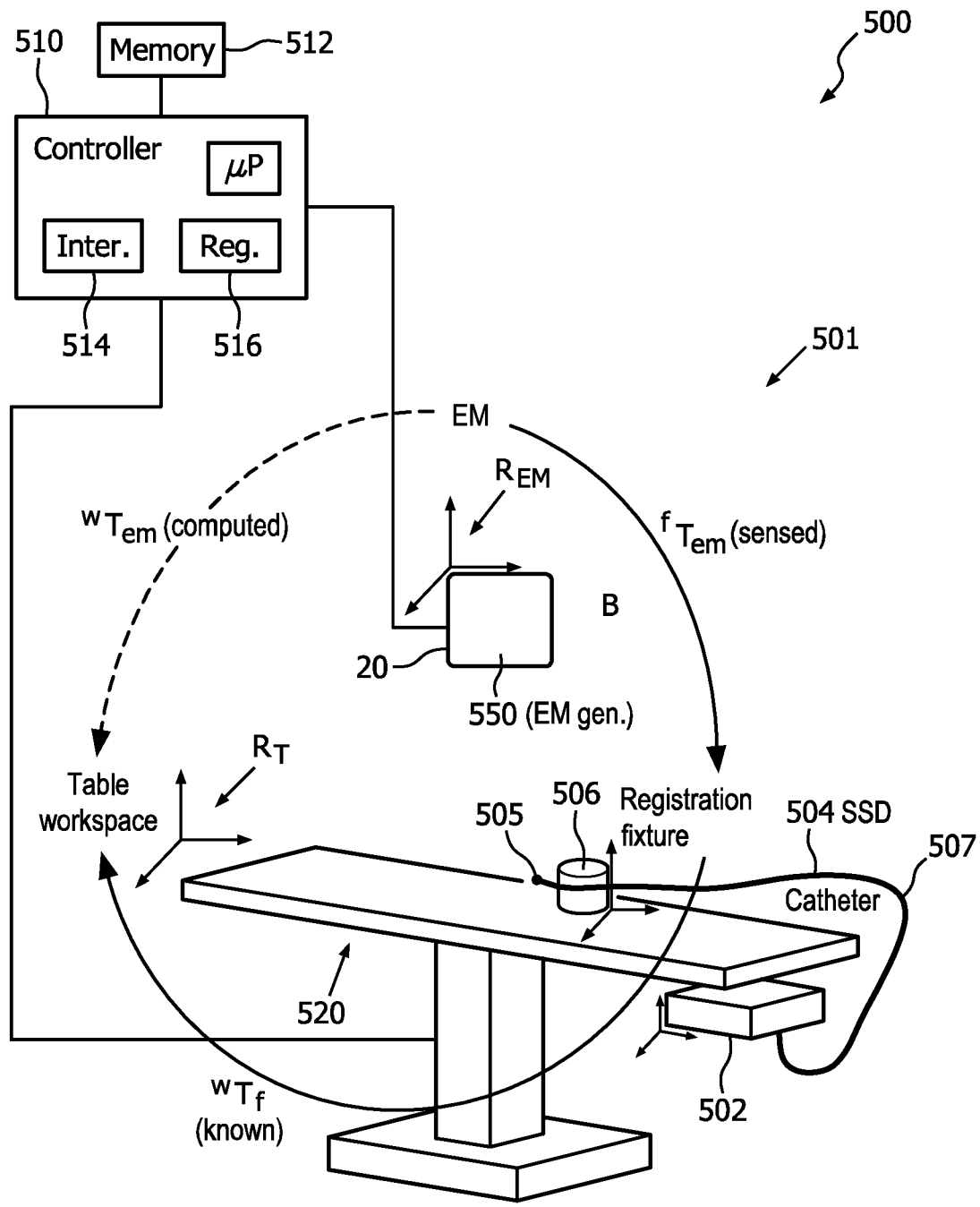
FIG. 5 shows a perspective front view of a portion of a shape sensing device (SSD) registration system operating in accordance with embodiments of the present system.

FIG. 5 shows a perspective front view 500 of a portion of an SSD registration system 501 (hereinafter system 501 for the sake of clarity) operating in accordance with embodiments of the present system. The system 501 may be similar to the system 101 and may include a device base 502, an SSD 504, a registration fixture 506, an RO such as a table 520, a controller 510, and a memory 512 which may be similar to the device base 102, the SSD 104, the registration fixture 106, the table 120, the controller 110, and the memory 112, respectively, of the system 101 of FIG. 1. However, the system 501 may include an electromagnetic (EM) field generator 550 having its own workspace/coordinate system (e.g., an EM space) $R_{EM}$ defining an EM coordinate system (e.g., EM space). Further, the SSD 504 may include catheter 507 with at least one EM sensor 505 which may be sequentially tracked in time relative to the workspace of the EM field generator 550.

The table 520 may be similar to the table 120 and may have its own workspace $R_T$.

The controller 510 may control the overall operation of the system 501 and may include one or more logic devices such as microprocessors, logic gates, switching devices, and/or the like. The controller 510 may include an interrogation module 514 and/or a registration module 516 that may be similar to the interrogation module 114 and/or a registration module 516.

The interrogation module 514 may be similar to the interrogation module 114 and may be operative to control the EM field generator 550 to track the at least one sensor 505 using an EM tracking technique.

The EM field generator 550 may be mounted in a workspace of the system 501 such as above the table 520 and may be operative to track one or more surgical instruments such as catheters, needles, and/or other flexible instruments that may be employed in within the workspace and to form corresponding SSDI which may include position information (including position and orientation) obtained using EM techniques. The EM field generator 550 may define a boundary (B) which may define a region in which the EM field generator 550 may accurately perform tracking. Accordingly, the registration fixture 506 may be placed within the boundary (B) so that position and/or and orientation measurements of the at least one sensor 505 within a channel of the registration fixture 506 may be accurate.

In the present embodiments, it will be assumed for the sake of clarity that the at least one sensor 505 may include a single sensor mounted at a distal end of the SSD 504 where position and/or orientation of the SSD 504 (forming the corresponding SSDI) is determined using time-sequential measurements obtained from the distal sensor 505, under the control of the controller 510, as the SSD 504 is moved in the RC of the registration fixture 506 and is sequentially tracked in time. However, without limitation it should be understood that at least one sensor 505 may include a plurality of sensors situated apart from each other along a length of the SSD 504. The EM field generator 550 may then selectively obtain position information from a plurality of sensors of the at least one sensor 505 substantially at the same time (e.g., synchronously) and form corresponding SSDI.

During an interrogation, the system 501 may interrogate the at least one sensor 505 of the SSD 504 sequentially over time to obtain position information from at least one sensor 505 and form corresponding SSDI. This SSDI may then be reconstructed to determine the path (P) of the channel. For example, as the SSD 504 traverses a channel (e.g., RC) of the registration fixture 506, the at least one sensor 505 may be tracked and a path traveled by the at least one sensor 505 may be tracked in the EM coordinate system and corresponding SSDI may be formed. The system may then recognize the path (P) (e.g., in the EM workspace) and match this path to a known path with a known fixture-to-workspace ($^wT_f$) transformation. The system may then perform a registration as will be described below with reference to the registration process.

Accordingly, the SSDI may include sufficient information to determine a path traversed by one or more portions of the SSD 504 over time, thus determining a shape of the SSD 504 at any time, such as for performing re-registration at any time. During a registration process, the SSDI 504 may be processed and information related to a known offset of the corresponding fixture-to-object pair (e.g., as set forth by the fixture-to-workspace transformation ($^wT_f$) of a corresponding fixture-to-object pair) may be obtained and processed to align a reference frame $R_{EM}$ of the EM field generator 550 with a desired reference frame of an RO such as a reference frame $R_T$ of the table 520 during a registration process performed in accordance with embodiments of the present system. Accordingly, the system 501 may be operative to align the reference frame $R_{EM}$ of the EM field generator 550 with a desired reference frame of an RO such as a reference frame $R_T$ of the table 520 (and/or other desired reference frames such as a patient reference frame) during, for example, a registration process performed in accordance with embodiments of the present system regardless of whether the position of the EM field generator 550 is known.

Thus, the registration performed in accordance with embodiments of the present system may allow the EM field generator 550 to be located in an unknown position and/or orientation relative to the (surgical) workspace (e.g., above the operating table 520). Navigation using EM-based instruments in a workspace may be simplified by registering and/or otherwise aligning the EM space with other objects situated in the workspace such as a surgical table, a patient, a catheter, a robotic surgical instrument, etc., and/or combination(s) thereof. The system 501 may include a boundary which may indicate a region in which the EM field generator 550 may be placed so that measurements through the registration fixture 506 may be valid.

Thus, embodiments of the present system may provide a registration fixture configured to have a known spatial relationship to the registrant object such as a table. The registration fixture may include a channel having a path through which a tracked instrument such as an SSD can be inserted and tracked using FORS and/or EM methods. The path may have a known relationship to the registration fixture, and thus to the registrant object such as the table. Embodiments of the present system further disclose a method to track the SSD as it traverses the registration fixture, so that a path measured in a coordinate system of a desired workspace such as EM space can be associated with the known identical path on the table to produce a registration in accordance with embodiments of the present system. Along with the registration fixture is a boundary that indicates the region in which the EM field generator must be placed so that measurements through the fixture may be valid.

FORS and EM registrations performed using the embodiments shown in FIGS. 1 and 5, respectively, will now be shown and described with reference to FIGS. 6 and 7, respectively.

Figure 6:
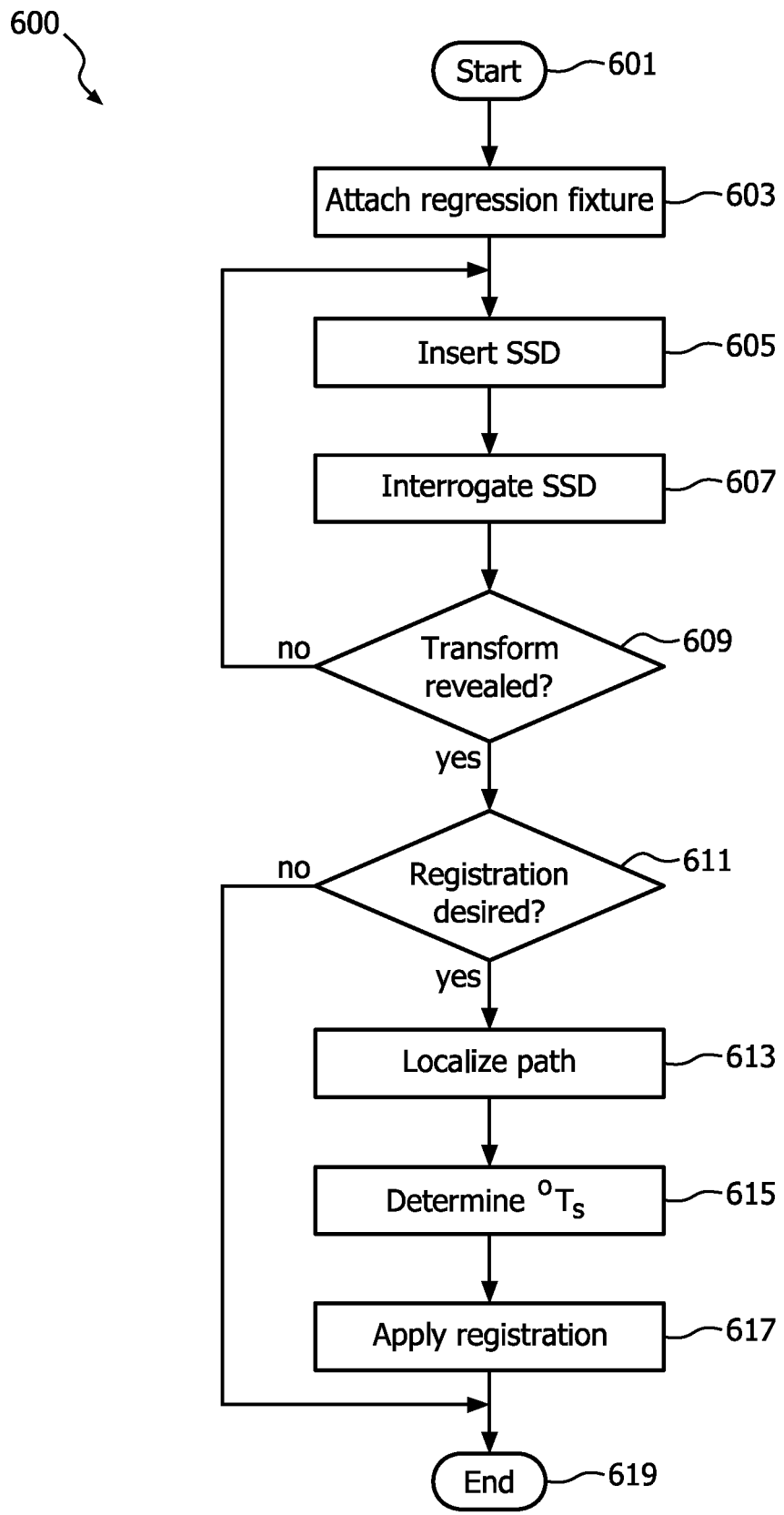
FIG. 6 shows a functional flow diagram performed by a process in accordance with embodiments of the present system.

FIG. 6 shows a functional flow diagram performed by a process 600 in accordance with embodiments of the present system. The process 600 may be performed using one or more processors, computers, controllers, etc., communicating over a network and may obtain information from, and/or store information to one or more memories which may be local and/or remote from each other. The process 600 may include one of more of the following acts. In accordance with embodiments of the present system, the acts of process 600 may be performed using one or more suitable coordinate registration systems operating in accordance with embodiments of the present system. Further, one or more of these acts may be combined and/or separated into sub-acts, as desired. Further, one or more of these acts may be skipped depending upon settings. Moreover, for the sake of clarity, the process will be described with reference to a single SSD of a registration system. However, it should be understood that the process may be repeated for each SSD in the registration system. In operation, the process may start during act 601 and then proceed to act 603.

During act 603, a registration fixture (hereinafter fixture) may be attached (e.g., by coupling) to a registrant object (hereinafter object) by the attachment mechanism. When properly attached, the fixture may be located in a desired known position and/or orientation relative to the object such that the position and/or orientation (e.g., depending upon 6D or 3D localization) may correspond with a fixture-to-object transformation ($^oT_f$) which may have been previously determined and/or stored in a memory of the system, where the object may have a workspace. Thus, the fixture-to-object transformation ($^wT_f$) may be the same as a fixture-to-workspace transformation ($^wT_f$), where the workspace refers to the workspace of the object. After completing act 603, the process may continue to act 605.

During act 605, the SSD may be fully or sufficiently inserted within a channel (defining a path (P)) of a registration fixture. The insertion of the SSD may be controlled by the system and/or by a user directly or via remote control. For example, a robotic manipulator may insert (or otherwise place) the SSD into a first end of the channel of a registration fixture attached to table and having a known position and/or orientation, until the SSD is at or extends from the second end of the channel. The robotic manipulator may operate independently of a user or may be controlled by a user, if desired. The user may be situated locally and/or remotely of the robotic manipulator. However, in yet other embodiments, the system may generate a user interface (UI) which may instruct a user to insert the SSD fully into the channel and render this UI on a display of the system. The user may then manually insert the SSD into the channel, if desired. After completing act 605, the process may continue to act 607.

During act 607, the process may interrogate the SSD to obtain SSDI from the SSD. The SSDI may contain information sufficient to determine a shape of the SSD. The SSDI may be synchronously obtained from a plurality of sensors of the SSDI. However, in yet other embodiments, the SSDI may be obtained from at least one sensor of the SSD such as a distal end EM sensor sequentially in time. For example, it is envisioned that the interrogation may include a plurality of interrogations over time and/or a single interrogation to acquire the SSDI. When the SSD is fully or sufficiently inserted within the channel, the process may detect the path (P) and/or the SSDI may include sufficient information to reveal a transformation of the registration fixture as will be discussed below with reference to act 609. After completing act 607, the process may continue to act 609.

During act 609, the process may determine whether a shape-to-fixture transformation ($^fT_s$) is revealed. Accordingly, if it is determined that the shape-to-fixture transformation ($^fT_s$) is revealed, the process may continue to act 611. However, if it is determined that the shape-to-fixture transformation ($^fT_s$) is not revealed, the process may repeat acts 605 and 607. The process may determine that a shape-to-fixture transformation ($^fT_s$) is revealed based upon a computation of the SSDI and/or comparison of the SSDI with one or more known shape-to-fixture transformations ($^fT_{s(known)}$) stored in a memory of the system. Accordingly, when as a result of the computation, the shape-to-fixture transformation ($^fT_s$) matches a known shape-to-fixture transformation ($^fT_{s(known)}$) of the one or more known shape-to-fixture transformations ($^fT_{s(known)}$), the process may determine that the shape-to-fixture transformation ($^fT_s$) is revealed. Alternatively, if as a result of the comparison, the shape-to-fixture transformation ($^fT_s$) does not match a known shape-to-fixture transformation ($^fT_{s(known)}$) of the one or more known a shape-to-fixture transformations ($^fT_{s(known)}$), the process may determine that the shape-to-(registration fixture) transformation ($^fT_s$) is not revealed. In other words, when a path (P) of a channel is detected, its fixture shape-to-fixture transformation ($^fT_s$) is revealed and the process may continue to act 611. Conversely, when a path (P) of a channel is not detected, its fixture shape-to-fixture transformation ($^fT_s$) is not revealed, and the process may repeat acts 605 and 607. Generally, in accordance with embodiments of the present system when the shape-to-fixture transformation ($^fT_s$) is not revealed, this will be assumed, for the sake of clarity, to be indicative of the SSD not being inserted sufficiently into the channel as opposed to the channel not being known.

During act 611, the process may determine whether registration is desired. Accordingly, if a registration is desired, the process may continue to act 613. However, if a registration is not desired, the process may continue to act 619 where the process may end.

This act may be performed so that a user may have an input on whether a registration may be performed. Accordingly, during this act, the process may generate and render a user interface (UI) on rendering device of the system such as a display requesting input from a user as to whether a perform a registration. The system may then determine whether to perform the registration based upon an input of the user. Alternatively, the system may have a default setting such as registration is desired (or alternatively, registration not desired) which may be selected when a timer elapses (e.g., after 20 seconds).

During act 613, the process may localize the path (P). More particularly, the system may exploit the provision of multiple sample points along the SSD to localize the path (P), and thus the registration fixture corresponding to the path (P). After completing act 613, the process may continue to act 615. In accordance with embodiments of the present system, during this act, all sample points may be examined initially to find the set of points whose pattern matches the pattern of the (known) path; in other words, only those points contained within the path. In accordance with embodiments of the present system, only these points (e.g., which may be referred to as path points) may then be used for registration. Of the points found to be path points, a continuum of points or subset of points may be used to compute the registration. For the continuum of points, known algorithms such as Iterative Closest Point (ICP) may be employed by the system. For the case of a subset of the path points, the particular subset may be selected based on the path features, such as the peaks and inflection points of a sine wave. These points may be used to compute the registration also by means known in art, such as Procrustes or least squares optimization.

For example, the path (P) may be localized and thus shape of the SSD determined synchronously based on a single measurement when multiple sensors are provided in the SSD, or sequentially in time when only one sensor (e.g., at the distal end of the SSD) is provided to track location of single sensor as the SSD is moved in the RC of the registration fixture.

During act 615, the system may determine a shape-to-object transformation ($^oT_s$) based upon the previously determined shape-to-fixture transformation ($^fT_s$) and the fixture-to-object transformation ($^oT_f$) using the following equation $^oT_s = {^oT_f} * {^fT_s}$. After completing act 615, the process may continue to act 617. The shape-to-object transformation ($^oT_s$) may be determined using any suitable method such as ICP, cross-correlation methods, least squares optimization, or the like.

During act 617, the process may apply the registration. Accordingly, a workspace of the registrant object such as a table (e.g., see, FIG. 1) may be registered to a reference workspace. After completing act 617, the process may continue to act 619, where it may end.

The registration process 600 may be initiated at the request of a user and/or automatically when certain events are detected by the system such as when an SSD is inserted into the channel or RC of registration fixture attached to the table and/or shaped as the path (P) of the channel. Accordingly, the system may interrogate the SSD at predefined intervals in time and/or space to detect this occurrence. It will be further appreciated that upon detecting that the SSD is situated in the path (P) or RC of the registration fixture attached to the table, the system may interrogate the SSD to obtain SSDI from one or more sensors of the SSD. It will be further appreciated the SSD may be inserted within a guide such as within a catheter, or attached to an outer surface of the catheter, as may be desired.

Figure 7:
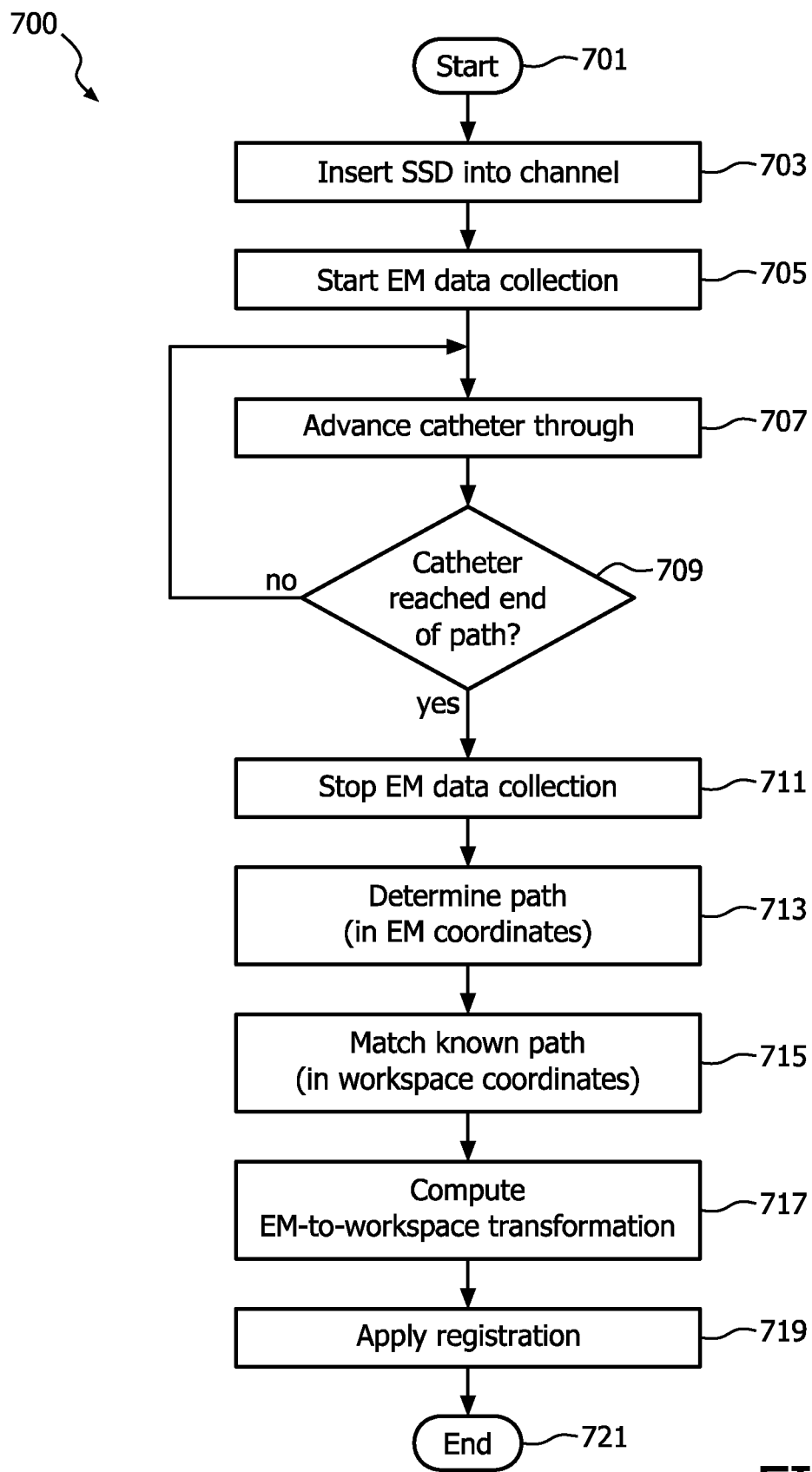
FIG. 7 shows a functional flow diagram performed by a process in accordance with embodiments of the present system.

FIG. 7 shows a functional flow diagram performed by a process 700 in accordance with embodiments of the present system. The process 700 may be performed using one or more processors, computers, controllers, etc., communicating over a network and may obtain information from, and/or store information to one or more memories which may be local and/or remote from each other. The process 700 may include one of more of the following acts. In accordance with embodiments of the present system, the acts of process 700 may be performed using one or more suitable coordinate registration systems operating in accordance with embodiments of the present system. Further, one or more of these acts may be combined and/or separated into sub-acts, as desired. Further, one or more of these acts may be skipped depending upon settings. Moreover, for the sake of clarity, the process will be described with reference to a single SSD of a registration system. However, it should be understood that the process may be repeated for each SSD in the registration system. In operation, the process may start during act 701 and then proceed to act 703.

During act 703, the system may be operative to control a robotic manipulator to insert an SSD having at least one sensor into a registration channel (hereinafter channel) of a registration fixture (hereinafter fixture for the sake of clarity) attached to a reference workspace or object such the table 520 shown in FIG. 5. Alternatively, the system may detect insertion of the SSD into the registration fixture by a user. For example, a sensor located at the channel (RC) of the registration fixture may detect insertion of the SSD, generate corresponding information and provide this information to a controller of the system to alert the controller that a registration process has begun. The SSD may be similar to the SSD 504 of FIG. 5 include at least one sensor such as an EM sensor located at a tip thereof and/or optical shape sensors positioned along a length thereof. After completing act 703, the process may continue to act 705.

During act 705, the process may begin EM data collection to obtain EM data from the at least one sensor of the SSD. Accordingly, the system may interrogate the at least one sensor of the SSD sequentially over time and form corresponding EM data which may be included in SSDI. The EM data may be collected by an EM generator having an EM workspace of the system. After completing act 705, the process may continue to act 707.

During act 707, the SSD may be advanced though the channel of the registration fixture. This process may performed automatically by a robotic manipulator which may further insert the SSD into the channel or manually by the user. During this act the process may continue to collect EM data so that a path of the at least one sensor of the SSD through the channel of the registration fixture may be tracked or otherwise traced over time. After completing act 707, the process may continue to act 709.

During act 709, it may be determined whether the SSD has reached the end of the (registration) channel. Accordingly, if it is determined that the SSD has reached the end of the registration channel, the process may continue to act 711. However, if it is determined that the SSD has not reached the end of the registration channel, the process may repeat act 707. Accordingly, the SSD may be further advanced in the channel. The system may determine that the SSD has reached the end of the channel by analyzing sensory feedback information such as a sensor at the end of the channel which may report that the SSD has reached the end of the channel and/or by analyzing the SSDI. It is also envisioned that it may be assumed that the SSD has reached the end of the channel when sufficient SDDI is collected. For example, if the SSDI contains sufficient information to recognize a path (P) of the channel, the process may determine that the SSD has reached the end of the channel.

During act 711, the process may stop the EM data collection which obtained the EM data from the at least one sensor of the SSD that was begun during act 705. Other functions of the EM generator may remain in operation independent of the current process. For example, the EM generator may track a plurality of objects within its workspace. After completing act 711, the process may continue to act 713.

During act 713, the process may determine a shape of the path (P) traveled by the at least one sensor within the channel. As the catheter has reached the end of the path, the EM data within the SSDI at this point may include sufficient information to identify the shape of the path (P) of the channel that the at least one sensor traversed. As the path has been identified, the process may reveal a corresponding EM-to-fixture transformation ($^{f}T_{em}$) which may be similar to and referred to as a shape-to-fixture transformation ($^{f}T_{s}$) discussed elsewhere herein. However, the shape may be determined using EM coordinates. After completing act 713, the process may continue to act 715.

During act 715, the process may match the identified path (P) with known path information to obtain a corresponding known fixture-to-workspace transformation ($^{w}T_{f}$) from a memory of the system. The fixture-to-workspace transformation ($^{w}T_{f}$) may have been previously determined and stored in a memory of the system in association with the fixture-workspace pair (FWP). After completing act 715, the process may continue to act 717. The fixture-to-workspace transformation ($^{w}T_{f}$) may be similar to the fixture-to-object transformation ($^{o}T_{f}$) discussed elsewhere in this document with the object being the table.

During act 717, the process may determine an EM-to-workspace transformation ($^{w}T_{em}$) based upon the above-determined EM-to-fixture transformation ($^{f}T_{s}$) (e.g., a shape-to-fixture transformation) and the matched fixture-to-workspace transformation ($^{w}T_{f}$) in accordance with the following equation: $^{w}T_{em} = {^{w}T_{f}} * {^{f}T_{em}}$. Accordingly, the process may compute the transformation between both sets of path information (e.g., obtained during act 713 and 715) using any suitable method such as ICP, cross-correlation methods or the like. After completing act 717, the process may continue to act 719. The EM-to-workspace transformation ($_{w}T_{em}$) may be similar to the shape-to-object transformation ($^{o}T_{s}$) discussed elsewhere with the object being the EM workspace (w) and the shape being the EM shape of the SSD inserted into the RC of a registration fixture and/or of a catheter inserted into a subject, obtained using at least one EM sensor, such as a coil at the distal end of the SSD and/or the catheter.

During act 719, the process may apply the registration and continue to act 721 where the process may end.

Figure 8:
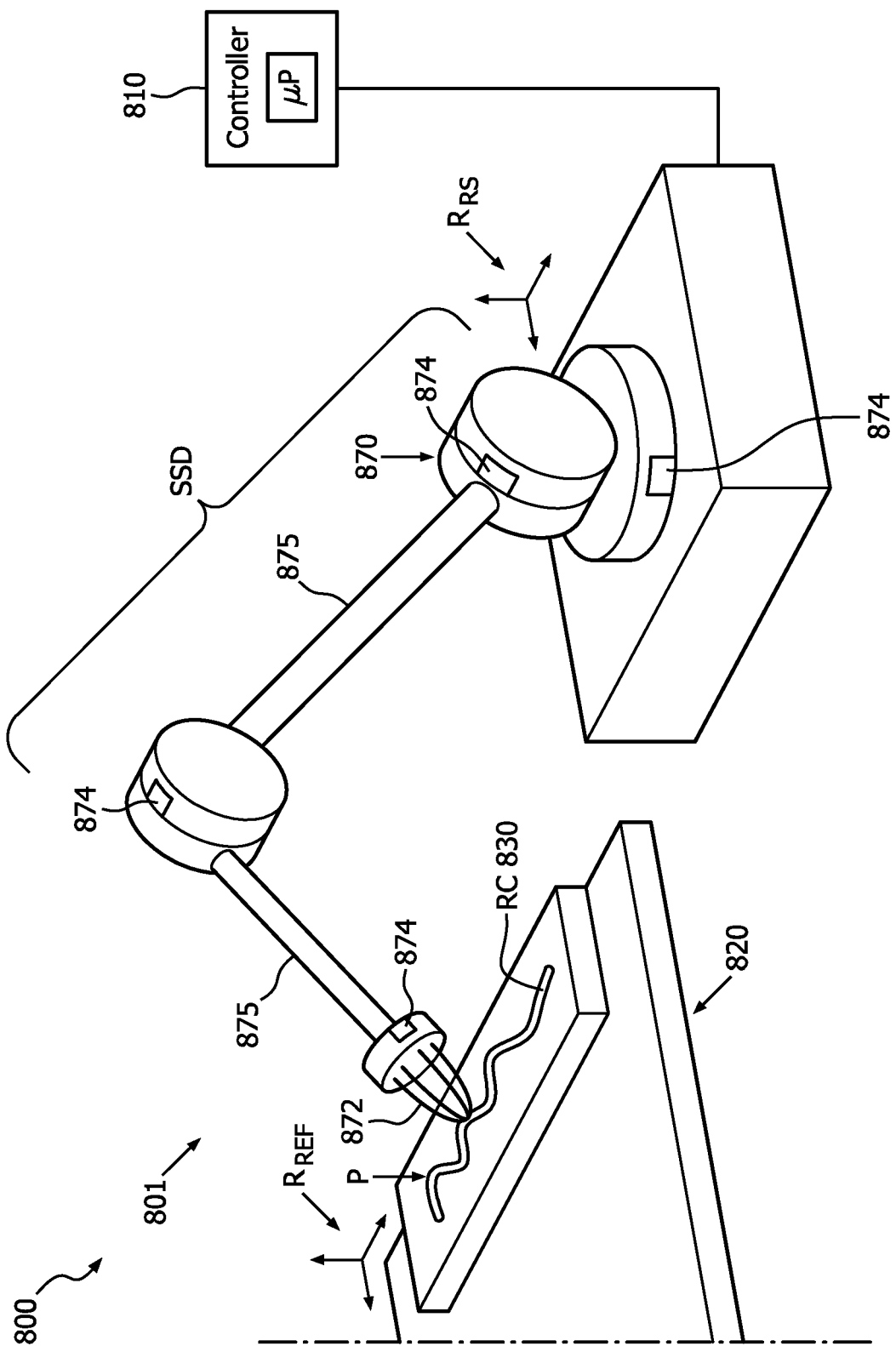
FIG. 8 shows a perspective front view of a portion of a registration system operating in accordance with embodiments of the present system.

FIG. 8 shows a perspective front view 800 of a portion of a registration system 801 (hereinafter system 801 for the sake of clarity) operating in accordance with embodiments of the present system. The system 801 may include a controller 810 which may be operative to register a robotic manipulator 870 in a workspace of a robotic system, which robotic workspace defines a coordinate system $R_{RS}$ to a reference workspace coordinate system $R_{REF}$ which may be in an unknown position relative to $R_{RS}$. The robotic manipulator 870 may include an end-effector 872 (e.g., a robotic end-effector) which may be guided (e.g., using any suitable method such as teleoperated, backdriven, system controlled, etc.) to trace a path (P) of a registration channel (RC) 830 on an object such as a table 820. The RC 830 may be outlined by any suitable shape so as to define the known path (P) such as a groove, a track, and/or other path indicators and may be identified by the system 801. This path P may be a known path and corresponding reference information, such as path information (PI), may be stored in a memory of the system. Sensors 874 such as joint encoders and the like may be coupled to the robotic manipulator 870 and may simultaneously and/or sequentially determine position and/or orientation of portions of the robotic manipulator 870 such as the position of joints, etc., and form corresponding position and/or orientation information such as SSDI related to the traced path (P). The controller 810 may then perform a registration based, at least in part, upon the SSDI and/or the PI. For example, the controller 810 may analyze the SSDI to determine a path traversed by the end-effector 872. Then, once this path is determined as set forth in the SSDI, corresponding shape-to-fixture ($^fT_s$) and transformation may be revealed, in both robot and workspace coordinates and registration may be completed. For example, during a registration process, the traced path (e.g., a sensed path such as may correspond with an object-to-workspace transformation ($^wT_o$) may be matched to a corresponding known fixture-to-workspace transformation ($^wT_f$) obtained from a memory of the system. Then the identical path may become known both in robotic and reference workspace coordinates, and can thus be registered. The path may include identifying surface features such as embossing and the like to further distinguish the path.

In accordance with embodiments of the present system, registration fixtures may primarily have a channel or path through which a tracked device (e.g., an SSD) traverses to trace out a pattern such as a sensed path. The pattern may then be matched against a known pattern (e.g., a known shape of a path) in a known position (including position and/or orientation information) to deduce a registration relative to an RO. In accordance with embodiments of the present system, the SSD may be flexible or rigid (c.f. SSD FIGS. 1 and 2 with SSD FIG. 8). Thus, generation of tracked patterns by the SSDs, however, need not be limited to insertion motions within channels accessible only by flexible instruments. For example, and without limitation, it may be desired to generate a tracked pattern using a rigid instrument (see, robotic manipulator FIG. 8) by, for example, manipulating the rigid instrument so as to pivot it about a post, slide it across a smooth surface with salient topographical features, and so forth. Thus, a role of the registration fixture may be to allow a tracked device to move in constrained and recognizable pattern, which may be detected and used for determining a registration.

Tracking a position of an SSD from, for example, the moment it enters the registration fixture and accumulating tracking of the path of the SSD as the traverses the registration fixture may be implemented in a straightforward manner. However, in some instances it may be more reliable and/or ergonomic to secure the SSD to the registration fixture and employ a mechanism on the registration fixture to maneuver the SSD in a predetermined way so as to trace a path (e.g., a sensed path). For example, the registration fixture may include actuators which may grasp one or more portions of the SSD and guide the SSD so that the SSD may sufficiently traverse the channel. Accordingly, it is envisioned that the registration fixture may include actuators which may augment path/motion traversal of the SSD under the control of a controller of the system.

It is further envisioned that registration workflow and/or accuracy may be enhanced by employing a registration fixture which may contain at least one tracking element. For example, it is envisioned that the registration fixture may contain a path for insertion of an EM-tracked catheter or the like. Once the catheter is inserted, a user or a controller of the registration fixture may slide a tracked slider which runs alongside the catheter path, and the system may track the slider instead of tracking the catheter (or SSD attached to or included in the catheter), with the knowledge that the generated path may have a shape that may be identical to that of a shape of the catheter (or other SSD) if the catheter were inserted with the path. Thus, the SSD may include a slider. This variant may enhance synchronization of a system to catheter path traversal.

In with yet other embodiments, multiple registration fixtures may be distributed, each in a known spatial relationship, across one or more workspaces. This approach may improve convenience by allowing the user to select a desired registration fixture that such as a most accessible registration fixture and/or a corresponding workspace. Each registration fixture may include a registration channel which may include a known unique pattern and/or path that may encode the identity of the path and/or registrations fixture, and therefore the corresponding path and/or registrations fixture position within a workspace.

In accordance with embodiments of the present system, the registration fixture may be designed based upon use and/or application. For example, for a surgical use, the registration fixture may be capable of being sterilized and/or may be coupled to a bed rail or imaging system in a predictable manner. Alternatively, the patient beds may be designed with a special slot to accommodate registration fixture such as disposable, sterilized registration fixtures and the like. Further, the registration fixture may be formed from a material such as plastic which may not block signals from the at least one sensor within the channel.

Although embodiments of the present system may have been described in the context of EM-guided navigation of surgical catheters, it should be understood that embodiments of the present system may include non-flexible instruments, non-surgical procedures, robotic surgery, and non-surgical robotic tasks in which registration is performed.

Figure 9:
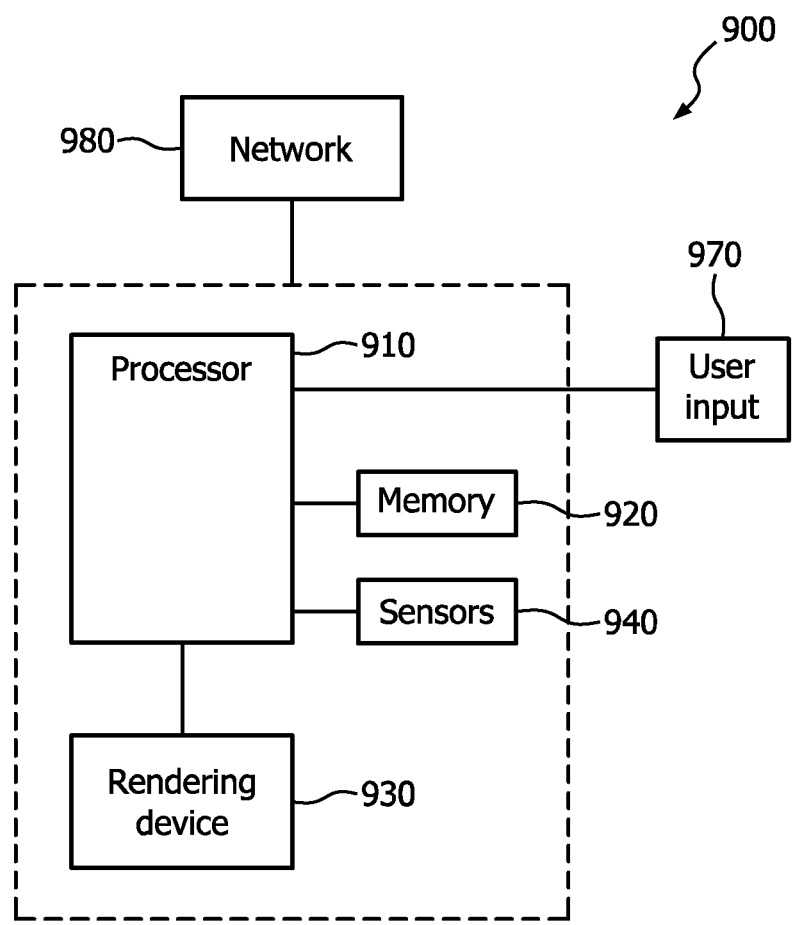
FIG. 9 shows a portion of a system in accordance with embodiments of the present system.

FIG. 9 shows a portion of a system 900 in accordance with embodiments of the present system. For example, a portion of the present system may include a processor 910 (e.g., a controller) operationally coupled to a memory 920, a user interface (UI) including a rendering device such as a display 930, sensors 940, and a user input device 970. The memory 920 may be any type of device for storing application data as well as other data related to the described operation. The application data and other data are received by the processor 910 for configuring (e.g., programming) the processor 910 to perform operation acts in accordance with the present system. The processor 910 so configured becomes a special purpose machine particularly suited for performing in accordance with embodiments of the present system.

The operation acts may include configuring a system by, for example, a registration system in accordance with system settings.

The processor 910 may control one or more power supplies to provide power to a registration system so that signals indicative of one or more coordinate systems may be generated. The processor 910, thereof may process received signals such as sensor information, transform these signals to location signals, and may generate content which may include image information (e.g., still or video images (e.g., video information)), data, and/or graphs that may be rendered on, for example, a UI of the system such as on the display 930, a speaker, etc. The content may include image information as may be generated by a medical imaging system or the like. Further, the content may then be stored in a memory of the system such as the memory 920 for later use. Thus, operation acts may include requesting, providing, and/or rendering of content. The processor 910 may render the content such as video information on a UI of the system such as a display of the system.

The user input 970 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 910 via any operable link such as a wired and/or wireless communication link. The user input device 970 may be operable for interacting with the processor 910 including enabling interaction within a UI as described herein. Clearly the processor 910, the memory 920, display 930, and/or user input device 970 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 920 or other memory coupled to the processor 910.

The program and/or program portions contained in the memory 920 may configure the processor 910 to implement the methods, operational acts, and functions disclosed herein. The memories may be distributed, for example between the clients and/or servers, or local, and the processor 910, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 910. With this definition, information accessible through a network is still within the memory, for instance, because the processor 910 may retrieve the information from the network for operation in accordance with the present system.

The processor 910 is operable for providing control signals and/or performing operations in response to input signals from the user input device 970 as well as in response to other devices of a network and executing instructions stored in the memory 920. The processor 910 may include one or more of a microprocessor, an application-specific or general-use integrated circuit(s), a logic device, etc. Further, the processor 910 may be a dedicated processor for performing in accordance with the present system or may be a general-purpose processor wherein only one of many functions operates for performing in accordance with the present system. The processor 910 may operate utilizing a program portion, multiple program segments, or may be a hardware device utilizing a dedicated or multi-purpose integrated circuit. Embodiments of the present system may provide imaging methods to acquire and/or reconstruct images. Suitable applications may include imaging systems such as MRI, (computer-aided tomography (CAT), ultrasound, optical, X-ray, systems, and/or combinations thereof. Further, embodiments of the present system may be ideally suited for surgical interventional techniques which may generate and render image and/or sensor information from one or more imaging systems (e.g., ultrasound, CT scans, MRI, etc.) having different coordinate systems in real-time with a unified coordinate system.

Figure 10:
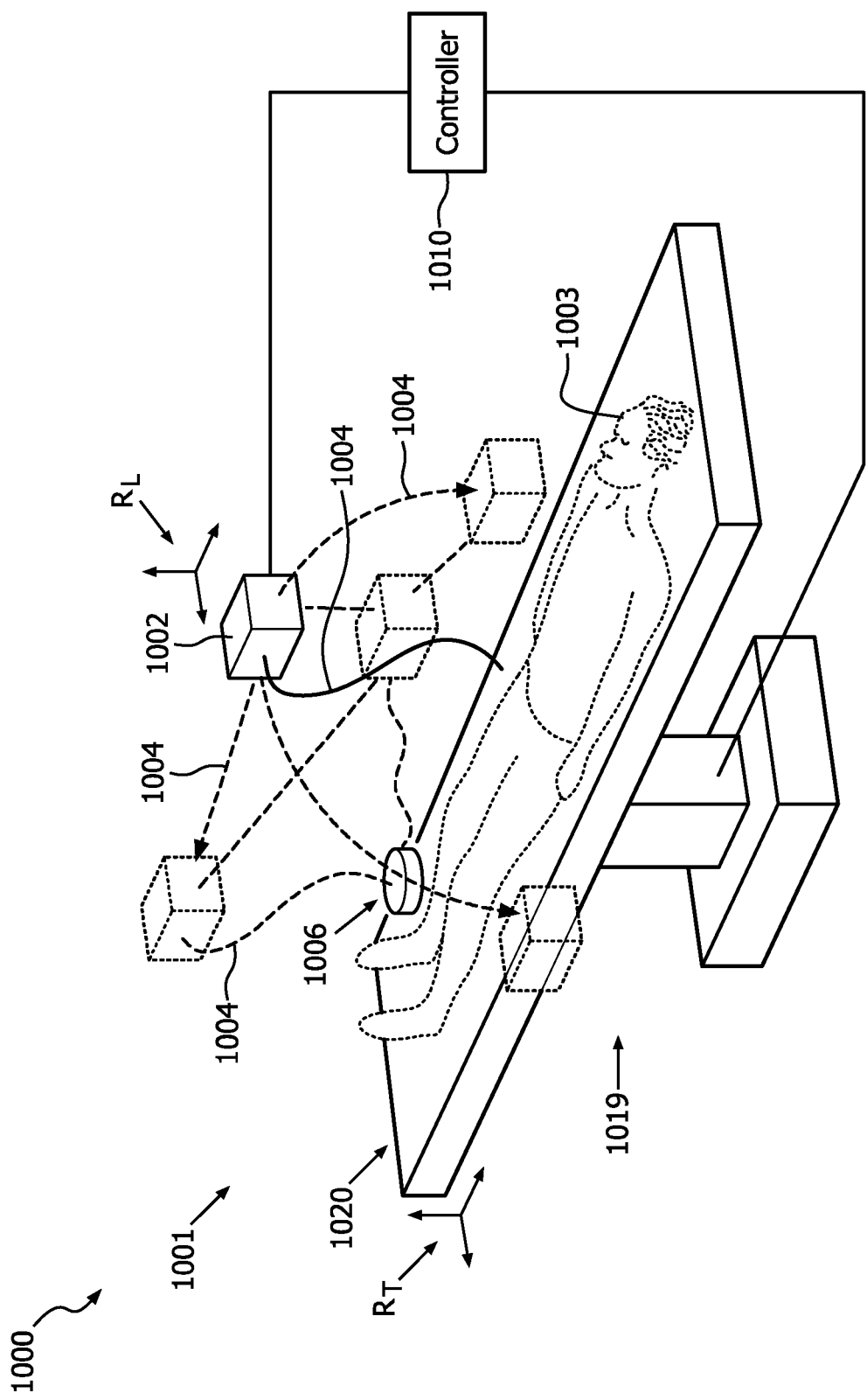
FIG. 10 shows a perspective front view of a portion of a registration system operating in accordance with embodiments of the present system.

FIG. 10 shows a perspective front view 1000 of a portion of a registration system 1001 (hereinafter system 1001 for the sake of clarity) operating in accordance with embodiments of the present system. The system 1001 may include one or more of a device base 1002, a shape sensing device (SSD) 1004 such as a shape sensing fiber (SSF), a registration fixture 1006, a registrant object 1019 (RO), such as a table 1020, and a controller 1010. During an interventional procedure, a patient 1003 may be situated upon the table 1020. The device base 1002 may be moved between various positions as may be necessary or desired by a clinician such as a surgeon during the interventional procedure with various locations shown by the dotted device bases. Initially, when relocated a workspace ($R_L$) of the device base 1002 may be unknown and may be registered easily using embodiments of the present system. For example, the SSD 1004 may be inserted into a registration channel of the registration fixture 1006 and, the system recognizing this may perform a registration of the workspace ($R_L$) of the device base 1002 to a workspace ($R_T$) of the table 1020. Accordingly, a user may easily and conveniently reposition the device base 1002 during the procedure.

Accordingly, embodiments of the present system provide an apparatus and method which may provide a registration fixture designed to have a known spatial relationship to a desired object for registration such as a surgical table, an EM field generator, etc. The registration fixture may include a path through which a tracked flexible fiber instrument may be inserted. The path may have a known relationship to the registration fixture, and thus to the object of registration such as a surgical table, an EM field generator, etc. In tandem with the fixture is a method that may track the SSD as it traverses the path of the registration fixture, so that the path measured in a desired coordinate system space such as EM space may be associated with the known identical coordinate system of the table (or objects with the same coordinate systems as the table such as a patient on the table) to produce registration. Along with the registration fixture is a boundary that indicates the region in which the EM field generator should be placed so that measurements through the registration fixture may be valid.

Further, embodiments of the present system may adjust reference frames or one or more objects-of-interest (OOI) in real-time for translational offsets as well as rotational offsets. Accordingly, embodiments of the present system may detect and adjust for angular discrepancies and/or other non-linear motion. It is further envisioned that embodiments of the present system may provide a system and method to streamline a registration process for coordinate systems of portions of a computer-assisted surgical (CAS) system (such as patient anatomy, operating table, imaging system(s), interventional devices, and the like). Shape sensing methods such as Fiber Optic RealShape™ (FORS) may be used to generate information for registration and/or operating workflow.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;
d) several "means" may be represented by the same item or hardware or software implemented structure or function;
e) any of the disclosed elements may be comprised of hardware portions (e.g., including discrete and integrated electronic circuitry), software portions (e.g., computer programming), and any combination thereof;
f) hardware portions may be comprised of one or both of analog and digital portions;
g) any of the disclosed devices or portions thereof may be combined together or separated into further portions unless specifically stated otherwise;
h) no specific sequence of acts or steps is intended to be required unless specifically indicated;
i) the term "plurality of" an element includes two or more of the claimed element, and does not imply any particular range of number of elements; that is, a plurality of elements may be as few as two elements, and may include an immeasurable number of elements; and
j) the term and/or and formatives thereof should be understood to mean that only one or more of the listed elements may need to be suitably present in the system in accordance with the claims recitation and in accordance with one or more embodiments of the present system.

What is claimed is:

1. A coordinate registration system, comprising:
a shape sensing device (SSD) comprising at least one position sensor for providing corresponding sensor information (SI) indicative of a position of the at least one position sensor;
a device base for positioning and/or orientating the SSD relative to a registrant object (RO), wherein a proximal end of the SSD is directly attached to the device base;
a registration fixture having an asymmetric channel, wherein the asymmetric channel extends through a body of the registration fixture, is configured to receive at least part of the SSD, and defines a registration path (P) having a predefined known shape, wherein the registration fixture is attached to the RO defining a workspace, and wherein a distal end of the SSD passes through the registration fixture; and
a controller configured to:
sense a shape of the SSD within the asymmetric channel based upon the SI obtained from the at least one position sensor when the at least one position sensor is situated within the asymmetric channel,
determine whether the sensed shape of the SSD within the asymmetric channel corresponds with the known shape of the registration path (P), and
perform a coordinate registration when it is determined that the sensed shape of the SSD within the asymmetric channel corresponds with the known shape of the registration path (P), wherein performing the coordinate registration comprises registering a coordinate system of the workspace relative to a coordinate system of the device base and a coordinate system of the registration fixture.

2. The coordinate registration system of claim 1, wherein to obtain the SI, the controller interrogates the at least one position sensor sequentially over time.

3. The coordinate registration system of claim 1, wherein the at least one position sensor of the SSD comprises a plurality of sensors and, to obtain the SI, the controller interrogates the plurality of sensors of the SSD synchronously over time.

4. The coordinate registration system of claim 1, wherein the controller is further configured to:
determine that the at least part of the SSD is within the asymmetric channel; and
interrogate the SSD to obtain the SI from the at least one position sensor in response to determining that the at least part of the SSD is within the asymmetric channel.

5. The coordinate registration system of claim 1, wherein during the coordinate registration, the controller is configured to determine a shape-to-fixture transformation ($^{f}T_{s}$) corresponding to the sensed shape of the SSD within the asymmetric channel.

6. The coordinate registration system of claim 5, wherein during the coordinate registration, the controller is further configured to obtain a fixture-to-workspace transformation ($^{w}T_{f}$) corresponding to the known shape of the registration path (P).

7. The coordinate registration system of claim 6, wherein during the coordinate registration, the controller is further configured to determine a shape-to-workspace transformation ($^{w}T_{s}$) by calculating: $^{w}T_{s}=^{w}T_{f}*^{f}T_{s}$.

8. The coordinate registration system of claim 6, further comprising:
at least one mechanical interlock configured to releasably attach the registration fixture to the RO at one or more of a position and orientation relative to the workspace of the RO which corresponds with the fixture-to-workspace transformation ($^{w}T_{f}$).

9. The coordinate registration system of claim 1, wherein the controller is configured to perform the coordinate registration without knowing a location of the device base.

10. The coordinate registration system of claim 1, wherein the asymmetric channel comprises a friction reducing interior surface and/or a friction increasing surface so as to attain a desired amount of friction when the SSD is inserted within the asymmetric channel during use.

11. The coordinate registration system of claim 1, wherein registration fixture further includes a clamping mechanism that, when engaged, configures the at least part of the SSD within the registration fixture into the predefined known shape.

12. A method for registering coordinate systems, the method being performed by at least one controller and comprising:
interrogating at least one position sensor of a shape sensing device (SSD), having a proximal end directly attached to a device base for positioning and/or orientating the SSD relative to a registrant object (RO) and a distal end inserted through an asymmetric channel in a registration fixture, to obtain sensor information (SI) indicative of at least one of a position of the at least one position sensor within the asymmetric channel, wherein the asymmetric channel is configured to receive at least part of a shape sensing device (SSD) and to define a registration path (P) having a predefined known shape, and wherein the registration fixture is attached to the RO defining a workspace;
sensing a shape of the SSD based upon the SI obtained from the at least one position sensor when the at least one position sensor is situated within the asymmetric channel;
determining whether the sensed shape of the SSD corresponds with the known shape; and performing a coordinate registration when it is determined that the sensed shape of the SSD within the asymmetric channel is determined to correspond with the known shape, wherein performing the coordinate registration comprises registering a coordinate system of the workspace relative to a coordinate system of the device base and a coordinate system of the registration fixture.

13. The method of claim 12, wherein interrogating the at least one position sensor of the SSD is performed sequentially over time.

14. The method of claim 12, wherein the at least one position sensor of the SSD comprises a plurality of sensors, and wherein interrogating the at least one position sensor of the SSD is performed substantially synchronously over time.

15. The method of claim 12, further comprising:
determining whether the at least part of the SSD is within the asymmetric channel; and
interrogating the SSD to obtain the SI from the at least one position sensor when it is determined that the at least part of the SSD is within the asymmetric channel.

16. The method of claim 12, wherein performing the coordinate registration comprises selecting a fixture-to-workspace transformation ($^{w}T_f$) corresponding to the known shape.

17. The method of claim 16, wherein performing the coordinate registration further comprises determining a shape-to-workspace transformation ($^{w}T_s$) by calculating: $^{w}T_s = {^{w}T_f} * {^{f}T}$.

18. A non-transitory computer readable medium comprising computer instructions which, when executed by a processor, configure the processor to perform acts of:

interrogating at least one position sensor of a shape sensing device (SSD), having a proximal end directly attached to a device base for positioning and/or orientating the SSD relative to a registrant object (RO) and a distal end inserted through an asymmetric channel in a registration fixture, to obtain sensor information (SI) indicative of at least one of a position of the at least one position sensor within the asymmetric channel, wherein the asymmetric channel is configured to receive at least part of the SSD and to define a registration path (P) having a predefined known shape;

determining a shape of the SSD based upon the SI obtained from the at least one position sensor when the at least one position sensor is situated within the asymmetric channel;

determining whether the determined shape of the SSD corresponds with the known shape selected from one or more known shapes; and performing a coordinate registration when it is determined that the sensed shape of the SSD within the asymmetric channel is determined to correspond with the known shape, wherein performing the coordinate registration comprises registering a coordinate system of the workspace relative to a coordinate system of the device base based on a and a coordinate system of the registration fixture.

19. The non-transitory computer readable medium of claim 18, wherein the computer instructions configure the processor to interrogate the at least one position sensor of the SSD sequentially over time.

* * * * *